US007517662B2

(12) United States Patent
Ridder et al.

(10) Patent No.: US 7,517,662 B2
(45) Date of Patent: Apr. 14, 2009

(54) METHOD FOR SOLUTION BASED DIAGNOSIS

(75) Inventors: Rüdiger Ridder, Schriesheim (DE); Wolfgang Rudy, Bretten (DE); Matthias Herkert, Heidelberg (DE); Marcus Trunk-Gehmacher, Heidelberg (DE); Anja Reichert, Nußloch (DE); Magnus Von Knebel Doeberitz, Heidelberg Ziegelhausen (DE)

(73) Assignee: MTM Laboratories, AG, Heidelberg (DE)

( * ) Notice: Subject to any disclaimer, the term of this patent is extended or adjusted under 35 U.S.C. 154(b) by 590 days.

(21) Appl. No.: 10/633,484

(22) Filed: Jul. 31, 2003

(65) Prior Publication Data

US 2004/0023288 A1 Feb. 5, 2004

(30) Foreign Application Priority Data

Aug. 1, 2002 (EP) .................................. 02017313

(51) Int. Cl.
*G01N 33/574* (2006.01)

(52) U.S. Cl. .......................... 435/7.23; 436/64; 530/350

(58) Field of Classification Search ................... 436/64, 436/501; 530/350, 387.3, 388.2; 435/7.92
See application file for complete search history.

(56) References Cited

U.S. PATENT DOCUMENTS

| 4,281,061 | A | | 7/1981 | Zuk et al. | |
|---|---|---|---|---|---|
| 5,976,799 | A | * | 11/1999 | O'Brien et al. | ................ 435/6 |
| 6,033,847 | A | | 3/2000 | Sherr et al. | |
| 6,316,208 | B1 | | 11/2001 | Roberts et al. | |
| 6,709,832 | B1 | * | 3/2004 | Von Knebel Doeberitz et al. | .......................... 435/7.23 |
| 2001/0039023 | A1 | | 11/2001 | Schubert | |
| 2002/0086288 | A1 | | 7/2002 | Bird et al. | |
| 2003/0157482 | A1 | | 8/2003 | Keesee et al. | |

FOREIGN PATENT DOCUMENTS

| EP | 0 723 156 | 12/1995 |
|---|---|---|
| EP | 1 217 377 | 12/2001 |
| EP | 1 388 734 B1 | 3/2004 |
| WO | WO 99/04238 | 7/1998 |

OTHER PUBLICATIONS

Litvinov SV et al. American Journal of Pathology 148(3): 865-875, 1996.*
Sano T et al. American Journal of Pathology 153(6): 1741-1748, 1998.*
Ranki M et al. Journal of Clinical Microbiology 28(9): 2076-2081, 1990.*
Aho et al. (J. Cell Sci. Apr. 1, 2002; 115 (Pt 7): 1391-1402).*
Bibbo et al. (Acta Cytologica. Jan.-Feb. 2002; 46 (1): 25-29).*
Grundhoefer et al. (Cytometry. Dec. 15, 2001; 46 (6): 340-344).*
Levy et al. (differentiation. Dec. 1988; 39 (3): 185-196).*
Kimmig et al. (J. Cancer Res. Clin. Oncol. 1995; 121: 107-114).*
von Knebel Deobertiz. (Dis. Markers. 2001; 17 (3): 123-128).*
Martens et al. (Cancer. Apr. 25, 1999; 87(2): 87-92).*
Smedts et al. (Am J Pathol. Mar. 1990; 136 (3): 657-668).*
Davey et al. (Arch. Pathol. Lab. Med. Feb. 2000; 124: 203-211).*
Day et al. (Am J Clin Pathol. 2002; 118: 41-46).*
Liggett et al. (J. Clin. Oncol. Mar. 1998; 16 (3): 1197-1206).*
He, et al., "Expression, Deletion And Mutation of p16 Gene in Human Gastric Cancer" *World J. of Gastroenterology* 7(4): 515-521 (2001).
Myung, et al., "Loss Of p16 And p27 Is Associated With Progression Of Human Gastric Cancer" *Cancer Letters* 153: 129-136 (2000).
Nakao et al., "Induction of p16 During Immortalization HPV 16 and 18 and Not During Malignant Transformation" *British J of Cancer* 75(10):1410-1416, 1997.
O'Nions, et al., "p73 Is Over-Expressed In Vulva Cancer Principally As The Δ2 Isoform" *British J. Cancer* 85(10):1551-1556 (Nov. 2001).
Sano, et al., "Overexpression Of P16 and P14ARF Is Associated With Human Papillomavirus Infection In Cervical Squamous Cell Carcinoma And Dysplasia" *Pathology Int.* 52:375-383 (May 2002).
Sherr, "The Ink4a/Arf Network In Tumor Suppression" *Nature Reviews Mol. Cell Bio* 2:731-737, (2001).
Takeuchi, et al., "Altered p16/MTSi/CDKN2 and Cycling D1/PRAD-1 Gene Expression Is Associated With The Prognosis of Squamous Cell Carcinoma of the Esophagus" *Clinical Cancer Research* 3:2229-2236, (1997).
Tsujie, et al., "Expression of Tumor Suppressor Gene p16INK4 Products in Primary Gastric Cancer" *Oncology* 58:126-136 (2000).
Betticher, et al., "Prognostic significance of CCND1 (cyclin D1) overexpression in primary resected non-small-cell lung cancer", *British J. of Cancer* 73: 294-300 (1996).
Browne, et al., "Analysis of the L1 Gene Product of Human Papillomavirus Type 16 by Expression in a Vaccinia Virus Recombinant", *J. gen. Virol.*, 69: 1263-73 (1988).
Carayol, et al., "NK cells differentiated from bone marrow, cord blood and peripheral blood stem cells exhibit similar phenotype and functions", *Eur. J. Immunol.* 28: 1991-2002 (1998).

(Continued)

*Primary Examiner*—Stephen L Rawlings
(74) *Attorney, Agent, or Firm*—Howrey LLP; Viola T. Kung

(57) ABSTRACT

This invention provides methods for improved diagnosis of medically relevant conditions by solution based biochemical testing procedures performed in solutions of test samples. The invention provides a method to substitute the cell based morphological information contained within the cytological and/or histological data of the test sample by molecular information obtainable from the solution, wherein the original test sample is dissolved and thus enables for accurate and reproducible assessment of medically relevant diagnosis from dissolved test samples. The method according to the invention comprises the steps of determining the levels of one or more disease markers associated with the condition to be diagnosed, determining the level of one or more normalization markers suitable to substitute the information related to morphological aspects of the sample, comparing and/or combining the data of the disease and normalization markers, and assessing diagnosis of a medically relevant condition.

12 Claims, 3 Drawing Sheets

OTHER PUBLICATIONS

Cattoretti, et al., "Monoclonal antibodies against recombinant parts of the Ki-67 antigen (MIB 1 and MIB 3) detect proliferating cells in microwave-processed formalin-fixed paraffin sections", *Journal of Pathology*, 168: 357-363 (1992).

Chilton, et al., "Estrogen Regulation of the Central Enzymes Involved in O- and N-Linked Glycoprotein Assembly in the Developing and the Adult Rabbit Endocervix", *Endocrinology*, 123(3): 1237-44 (1988).

de Boer, et al., "Changing Roles of Cadherins and Catenins during Progression of Squamous Intraepithelial Lesions in the Uterine Cervix", *American Journal of Pathology*, 155(2): 505-15 (1999).

Di Loreto et al., "Different binding to squamous and columnar epithelium of the uterine cervix as a marker of epithelial differentiation", *Bas. Appl. Histochem.* 31: 143-52 (1987).

Epenetos, et al., "Use of Two Epithelium-Specific Monoclonal Antibodies for Diagnosis of Malignancy in Serous Effusions", *The Lancet*, 1004-7 (1982).

Geradts, et al., "Immunohistochemical Detection of the Cyclin-dependent Kinase Inhibitor 2/Multiple Tumor Suppressor Gene 1 (CDKN2/MTS1) Product $p16^{INK4A}$ in Archival Human Solid Tumors: Correlation with Retinoblastoma Protein Expression", *Cancer Research* 55: 60066-11 (1995).

Grundhoefer, et al., "Determination of Liquid-Based Cervical Cytology Specimen Adequancy Using Cellular Light Scatter and Flow Cytometry", *Cytometry(Communications in Clinical Sytometry)*, 46: 340-4 (2001).

Guillou, et al., "Squamous Cell Carcinoa of the Lung in a Nonsmoking, Monirradiated Patient with Juvenile Laryngotracheal Papillomatosis", *The American Journal of Surgical Pathology*, 15(9) 891-8 (1991).

Hamid, et al., "Detection of Human Probombesin mRNA in Neuroendocrine (Small Cell) Carcinoma of the Lung", *Cancer*, 63:266-71 (1989).

Harada, et al., "Phenotypic Difference of Normal Plasma Cells from Mature Myeloma Cells", *Blood*, 81(10): 2658-63 (1993).

Heid, et al., "Cell type-specific desmosomal plaque proteins of the plakoglobin family: plakophilin 1 (band 6 protein)", *Differentiation*, 58: 113-31 (1994).

Hermann, et al., Reduced LAK Cytotoxicity of Peripheral Blood Mononuclear Cells in Patients with Bladder Cancer: Decreased LAK Cytotoxicity Caused by a Low Incidence of CD56+ and CD57+ Mononuclear Blood Cells.

Hirama, et al., "$p16$ (CDKN2/Cylin-dependent Kinase-+ inhibitor/ Multiple Tumor Suppressor-1) Gene Is Not Altered in Uterine Cervical Carcinomas or Cell Lines", *Modern Pathology*, 9(1) 26-31 (1996).

Iftner, et al., "Involvement of Human Papillomavirus Type 8 Genes E6 and E7 in Transformation and Replication", *Journal of Virology*, 62(10): 3655-61 (1988).

Jones, et al., Detection of T and B Cells in Many Animal Species Using Cross-Reactive Anti-Peptide Antibodies. *The Journal of Immunology*, 150: 5429-35 (1993).

Kelley, et al., "CDKN2 in HPV-Positive and HPV-Negative Cerival-Carcinoma Cell Lines", *Int. J. Cancer*, 63: 226-30 (1995).

Kim, et al., "Absence of $p15^{INK4B}$ and $p16^{INK4A}$ Gene Alterations in Primary Cervical Carcinoma Tisues and Cell Lines with Human Papillomavirus Infection", *Gynecologic Oncology*, 70: 75-9 (1998).

Kim, et al., "Underexpression of Cyclin-Dependent Kinase (CDK) Inhibitors in Cervical Carcinoma", *Gynecologic Oncology*, 71: 38-45 (1998).

Klaes, et al., "Overexpression of $p16^{INK4A}$ as a Specific Marker for Dysplastic and Neoplastic Epithelial Cells of the Cervix Uteri", *Int. J. Cancer*, 92: 276-284 (2001).

Koch, et al., "Specificity of antibodies to the purified Con A acceptor glycoproteins of cultured tumour cells", *Br. J. Cancer*, 53: 13-22 (1986).

Kommoss, et al., Inhibin-$_\alpha$. CD99, HEA125, PLAP, and Chromogranin Immunoreactivity in Testicular Neoplasms and the Androgen Insensitivity Syndrome, *Human Pathology*, 31(9): 1055-61 (2000).

Larsson, et al., Tissue Plasminogen Activator and Urokinase in Normal, Dysplastic and Cancerous Squamous Epithelium of the Uterine Cervix, *Thrombosis and Haemostasis*, 58(3): 822-6 (1987).

Latza, et al., "Ber-EP4: new monoclonal antibody which distinguishes epithelia from mesothelia", *J. Clin Pathol*, 43: 213-9 (1990).

Mason, et al., "Rapid Communication", *American Journal of Pathology*, 136(6) 1215-22 (1990).

Mendoza-Rodriguez, et al., El gen supresor de tumors $p53$: mecanismos de acción en la proliferación y muerte cellular, *Rincón Del Residente*, 53(3): 266-73 (2001).

Milde-Langosch, et al., "P16/MTS1 and $p$RB expression in endometrial carcinomas", *Virchows Arch*, 434: 23-8 (1999).

Milde-Langosch, et al., "$p16/MTS1$ Inactivation in Ovarian Carcinomas: High Frequency of rEduced Protein expression Associated with Hyper-Methylation or Mutation in Endometroid and Mucinous Tumours", *Int. J. Cancer*, 79: 61-5 (1998).

Mistretta, et al., "Isolation of a Carcino-Embryonic-Antigen (CEA) from a Liver Metastasis of Primary Adenocarcinoma of the Colon and Preparation of the Specific Antiserum", *Specialia*, 1209-10 (1974).

Mujica ven Herckenrode, et al., Antibodies specific for HeLa glycoprotein antigens are also specific for human endocervical epithelium, *Br. J. Cancer*, (1988).

Nair, et al., "Involucrin and Tumor Progression in the Uterine Cervix", *Pathobiology*, 64: 333-8 (1996).

Nuovo, et al., "In situ detection of the hypermethylation-induced inactivation of the $p16$ gene as a early event in oncogenesis", *PNAS*, 96(22): 12754-9 (1999).

Pagani, et al., "Expression of the Gastrin-Releasing Peptide Gene in Carcinomas of the Breast", *Int. J. Cancer* 47: 371-5 (1991).

Rogers, et al., "A Monoclonal Antibody Against a CEA-related Antigen Expressed on HT29 Colon Tumour Cells*", *J. Cancer Clinic. Oncology*, 20(10): 1279-86 (1981).

Sano, et al., "Expression Status of $p16$ Protein Is Associated with Human Papillomavirus Oncogenic Potential in Cervical and Genital Lesions", *American Journal of Pathology*, 153(6): 1741-8 (1998).

Sano, et al., "Immunohistochemical overexpression of $p$ 16 protein associated with intact retinoblastoma protein expression in cervical cancer and cervical intraepithelial neoplasia", *Pathology International*, 48: 580-5 (1998).

Serrano, et al., "A new regulatory motif in cell-cycle control causing specific inhibition of cyclin D/CDK4", *Nature*, 366: 704-7 (1993).

Shigemasa, et al., "$p16$ Overexpression: A Potential Early Indicator of Transformation in Ovarian Carcinoma", *J. Soc. Gynecol Invest.*, 4(2): 95-102 (1997).

Shim, et al., "Profiling of Differentially Expressed Genes in Human Primary Cervical Cancer by Complementary DNA Expression Array", *Clinical Cancer Research*, 4: 3045-50 (1998).

Smedts, et al., "Changing Patterns of Keratin Expressioin During Progressioin of Cervical Intraepithelial Neoplasia", *American Journal of Pathology*, 136(3): 657-68 (1990).

Smith, et al., "Cytochemical Demostration of Oxidative Damage in Alzheimer Disease by Immunochemical Enhancement of the Carbonyl Reaction with 2,4-Dinitrophenylhydrazine", *The J. of Histochemistry & Cytochemistry*, 46(6): 731-5 (1998).

Southern, et al., "Los of Cytokeratin 14 Expression Is Related to Human Papillomavirus Type and Lesion Grade in Squamous Intraepithelial Lesions of the Cervix", *Human Pathology*, 32(12): 1351-5 (2001).

Tam, et al., "Differential Expression and Cell Cycle Regulation of the Cyclin-dependent Kinase 4 Inhibitor $p16^{INK4}$", *Cancer Research*, 54: 1816-20 (1994).

Tashiro, et al., "Immunohistochemical Study of Mucin Carbohydrates and Core Proteins in Human Ovarian Tumors", *Human Pathology*, 25(4): 364-72 (1994).

van der Poel, et al., "Can biological marker replace cyctoscopy? An update", *Current Opinion in Urology*, 11:503-9 (2001).

Versura, "Detection of mucus glycoconjugates in human cervical epithelium by lectin-colloidal gold technique in transmission electron microscopy", *Bas. Appl. Histochem.*, 32: 219-27 (1998).

Waseem, et al., "Monoclonal antibody analysis of the proliferating cell nuclear antigen (PCNA)—Structrual conservation and the detection of a nucleolar form", *J. of Cell. Science*, 96: 121-9 (1990).

Wong, et al., "Methylation of $p16^{INK4A}$ in primary gynecologic malignancy", *Cancer Letters*, 136: 231-5 (1999).

Wong, et al., $p16^{INK4}$ and $p15^{INK4B}$ Alterations in Primary Gynecologic Malignancy, *Gynecologic Oncology* 65: 319-24 (1997).

Zimmer, et al,., "Proliferating Cell Nuclear Antigen (PCNA) in Atypical and Malignant Meningiomas", *Path. Res. Pract.* 188: 951-8 (1992).

* cited by examiner

SEQUENCE LISTING

```
<160> NUMBER OF SEQ ID NOS: 8

<210> SEQ ID NO 1
<211> LENGTH: 745
<212> TYPE: PRT
<213> ORGANISM: Homo sapiens
<220> FEATURE:
<221> NAME/KEY: misc_feature
<222> LOCATION: (1)..(745)
<223> OTHER INFORMATION: gamma-Catenin, Swissprot Accession Q86W21

<400> SEQUENCE: 1
```

-continued

```
Met Glu Val Met Asn Leu Met Glu Gln Pro Ile Lys Val Thr Glu Trp
1               5                   10                  15

Gln Gln Thr Tyr Thr Tyr Asp Ser Gly Ile His Ser Gly Ala Asn Thr
                20                  25                  30

Cys Val Pro Ser Val Ser Ser Lys Gly Ile Met Glu Glu Asp Glu Ala
            35                  40                  45

Cys Gly Arg Gln Tyr Thr Leu Lys Lys Thr Thr Thr Tyr Thr Gln Gly
    50                  55                  60

Val Pro Pro Ser Gln Gly Asp Leu Glu Tyr Gln Met Ser Thr Thr Ala
65                  70                  75                  80

Arg Ala Lys Arg Val Arg Glu Ala Met Cys Ser Gly Val Ser Gly Glu
                85                  90                  95

Asp Ser Ser Leu Leu Leu Ala Thr Gln Val Glu Gly Gln Ala Thr Asn
                100                 105                 110

Leu Gln Arg Leu Ala Glu Pro Ser Gln Leu Leu Lys Ser Ala Ile Val
            115                 120                 125

His Leu Ile Asn Tyr Gln Asp Asp Ala Glu Leu Ala Thr Arg Ala Leu
    130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Val Val Arg Thr
            180                 185                 190

Met Gln Asn Thr Ser Asp Leu Asp Thr Ala Arg Cys Thr Thr Ser Ile
    195                 200                 205

Leu His Asn Leu Ser His His Arg Glu Gly Leu Leu Ala Ile Phe Lys
    210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
            245                 250                 255

Gln Glu Gly Ala Lys Met Ala Val Arg Leu Ala Asp Gly Leu Gln Lys
            260                 265                 270

Met Val Pro Leu Leu Asn Lys Asn Asn Pro Lys Phe Leu Ala Ile Thr
    275                 280                 285

Thr Asp Cys Leu Gln Leu Leu Ala Tyr Gly Asn Gln Glu Ser Lys Leu
    290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
            340                 345                 350

Gly Met Gln Ala Leu Gly Lys His Leu Thr Ser Asn Ser Pro Arg Leu
    355                 360                 365

Val Gln Asn Cys Leu Trp Thr Leu Arg Asn Leu Ser Asp Val Ala Thr
    370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
            405                 410                 415

Asn Leu Thr Cys Asn Asn Ser Lys Asn Lys Thr Leu Val Thr Gln Asn
```

-continued

```
                420                 425                 430
Ser Gly Val Glu Ala Leu Ile His Ala Ile Leu Arg Ala Gly Asp Lys
            435                 440                 445

Asp Asp Ile Thr Glu Pro Ala Val Cys Ala Leu Arg His Leu Thr Ser
        450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
            500                 505                 510

Ala Asn His Ala Pro Leu Gln Glu Ala Val Ile Pro Arg Leu Val
        515                 520                 525

Gln Leu Leu Val Lys Ala His Gln Asp Ala Gln Arg His Val Ala Ala
    530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
            580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
    610                 615                 620

Gly Ala Ser Ala Pro Leu Met Glu Leu Leu His Ser Arg Asn Glu Gly
625                 630                 635                 640

Thr Ala Thr Tyr Ala Ala Ala Val Leu Phe Arg Ile Ser Glu Asp Lys
                645                 650                 655

Asn Pro Asp Tyr Arg Lys Arg Val Ser Val Glu Leu Thr Asn Ser Leu
            660                 665                 670

Phe Lys His Asp Pro Ala Ala Trp Glu Ala Ala Gln Ser Met Ile Pro
        675                 680                 685

Ile Asn Glu Pro Tyr Gly Asp Asp Leu Asp Ala Thr Tyr Arg Pro Met
    690                 695                 700

Tyr Ser Ser Asp Val Pro Leu Asp Pro Leu Glu Met His Met Asp Met
705                 710                 715                 720

Asp Gly Asp Tyr Pro Ile Asp Thr Tyr Ser Asp Gly Leu Arg Pro Pro
                725                 730                 735

Tyr Pro Thr Ala Asp His Met Leu Ala
            740                 745

<210> SEQ ID NO 2
<211> LENGTH: 314
<212> TYPE: PRT
<213> ORGANISM: Homo sapiens
<220> FEATURE:
<221> NAME/KEY: misc_feature
<222> LOCATION: (1)..(314)
<223> OTHER INFORMATION: Ep-Cam, Swissprot Accession P16422

<400> SEQUENCE: 2

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30
```

```
Lys Leu Ala Val Asn Cys Phe Val Asn Asn Arg Gln Cys Gln Cys
            35                  40                  45

Thr Ser Val Gly Ala Gln Asn Thr Val Ile Cys Ser Lys Leu Ala Ala
 50                  55                  60

Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
                 85                  90                  95

Pro Asp Cys Asp Glu Ser Gly Leu Phe Lys Ala Lys Gln Cys Asn Gly
                100                 105                 110

Thr Ser Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Met Ala Val Val Ala Gly Ile Val Val Leu Val Ile
            275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 3
<211> LENGTH: 882
<212> TYPE: PRT
<213> ORGANISM: Homo sapiens
<220> FEATURE:
<221> NAME/KEY: misc_feature
<222> LOCATION: (1)..(882)
<223> OTHER INFORMATION: E-Cadherin, Swissprot Accession P12830

<400> SEQUENCE: 3

Met Gly Pro Trp Ser Arg Ser Leu Ser Ala Leu Leu Leu Leu Leu Gln
 1               5                  10                  15

Val Ser Ser Trp Leu Cys Gln Glu Pro Glu Pro Cys His Pro Gly Phe
                20                  25                  30

Asp Ala Glu Ser Tyr Thr Phe Thr Val Pro Arg Arg His Leu Glu Arg
            35                  40                  45

Gly Arg Val Leu Gly Arg Val Asn Phe Glu Asp Cys Thr Gly Arg Gln
 50                  55                  60
```

-continued

```
Arg Thr Ala Tyr Phe Ser Leu Asp Thr Arg Phe Lys Val Gly Thr Asp
 65              70                  75                  80

Gly Val Ile Thr Val Lys Arg Pro Leu Arg Phe His Asn Pro Gln Ile
                 85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
```

```
                     485                 490                 495
Glu Asp Phe Gly Val Gly Gln Glu Ile Thr Ser Tyr Thr Ala Gln Glu
                500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
                580                 585                 590

Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
        690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
                740                 745                 750

Tyr Tyr Tyr Asp Glu Glu Gly Gly Gly Glu Glu Asp Gln Asp Phe Asp
            755                 760                 765

Leu Ser Gln Leu His Arg Gly Leu Asp Ala Arg Pro Glu Val Thr Arg
        770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
                820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp

<210> SEQ ID NO 4
<211> LENGTH: 906
```

```
<212> TYPE: PRT
<213> ORGANISM: Homo sapiens
<220> FEATURE:
<221> NAME/KEY: misc_feature
<222> LOCATION: (1)..(906)
<223> OTHER INFORMATION: Alpha-1 Catenin, Swissprot Accession P35221

<400> SEQUENCE: 4

Met Thr Ala Val His Ala Gly Asn Ile Asn Phe Lys Trp Asp Pro Lys
1               5                   10                  15

Ser Leu Glu Ile Arg Thr Leu Ala Val Glu Arg Leu Leu Glu Pro Leu
            20                  25                  30

Val Thr Gln Val Thr Thr Leu Val Asn Thr Asn Ser Lys Gly Pro Ser
        35                  40                  45

Asn Lys Lys Arg Gly Arg Ser Lys Lys Ala His Val Leu Ala Ala Ser
    50                  55                  60

Val Glu Gln Ala Thr Glu Asn Phe Leu Glu Lys Gly Asp Lys Ile Ala
65                  70                  75                  80

Lys Glu Ser Gln Phe Leu Lys Glu Glu Leu Val Ala Ala Val Glu Asp
                85                  90                  95

Val Arg Lys Gln Gly Asp Leu Met Lys Ala Ala Ala Gly Glu Phe Ala
            100                 105                 110

Asp Asp Pro Cys Ser Ser Val Lys Arg Gly Asn Met Val Arg Ala Ala
        115                 120                 125

Arg Ala Leu Leu Ser Ala Val Thr Arg Leu Leu Ile Leu Ala Asp Met
    130                 135                 140

Ala Asp Val Tyr Lys Leu Leu Val Gln Leu Lys Val Val Glu Asp Gly
145                 150                 155                 160

Ile Leu Lys Leu Arg Asn Ala Gly Asn Glu Gln Asp Leu Gly Ile Gln
                165                 170                 175

Tyr Lys Ala Leu Lys Pro Glu Val Asp Lys Leu Asn Ile Met Ala Ala
            180                 185                 190

Lys Arg Gln Gln Glu Leu Lys Asp Val Gly His Arg Asp Gln Met Ala
        195                 200                 205

Ala Ala Arg Gly Ile Leu Gln Lys Asn Val Pro Ile Leu Tyr Thr Ala
    210                 215                 220

Ser Gln Ala Cys Leu Gln His Pro Asp Val Ala Ala Tyr Lys Ala Asn
225                 230                 235                 240

Arg Asp Leu Ile Tyr Lys Gln Leu Gln Gln Ala Val Thr Gly Ile Ser
                245                 250                 255

Asn Ala Ala Gln Ala Thr Ala Ser Asp Asp Ala Ser Gln His Gln Gly
            260                 265                 270

Gly Gly Gly Gly Glu Leu Ala Tyr Ala Leu Asn Asn Phe Asp Lys Gln
        275                 280                 285

Ile Ile Val Asp Pro Leu Ser Phe Ser Glu Glu Arg Phe Arg Pro Ser
    290                 295                 300

Leu Glu Glu Arg Leu Glu Ser Ile Ile Ser Gly Ala Ala Leu Met Ala
305                 310                 315                 320

Asp Ser Ser Cys Thr Arg Asp Asp Arg Arg Glu Arg Ile Val Ala Glu
                325                 330                 335

Cys Asn Ala Val Arg Gln Ala Leu Gln Asp Leu Leu Ser Glu Tyr Met
            340                 345                 350

Gly Asn Ala Gly Arg Lys Glu Arg Ser Asp Ala Leu Asn Ser Ala Ile
        355                 360                 365

Asp Lys Met Thr Lys Lys Thr Arg Asp Leu Arg Arg Gln Leu Arg Lys
```

```
            370             375             380
Ala Val Met Asp His Val Ser Asp Ser Phe Leu Glu Thr Asn Val Pro
385                 390                 395                 400

Leu Leu Val Leu Ile Glu Ala Ala Lys Asn Gly Asn Glu Lys Glu Val
                405                 410                 415

Lys Glu Tyr Ala Gln Val Phe Arg Glu His Ala Asn Lys Leu Ile Glu
                420                 425                 430

Val Ala Asn Leu Ala Cys Ser Ile Ser Asn Asn Glu Glu Gly Val Lys
                435                 440                 445

Leu Val Arg Met Ser Ala Ser Gln Leu Glu Ala Leu Cys Pro Gln Val
450                 455                 460

Ile Asn Ala Ala Leu Ala Leu Ala Ala Lys Pro Gln Ser Lys Leu Ala
465                 470                 475                 480

Gln Glu Asn Met Asp Leu Phe Lys Glu Gln Trp Glu Lys Gln Val Arg
                485                 490                 495

Val Leu Thr Asp Ala Val Asp Asp Ile Thr Ser Ile Asp Asp Phe Leu
                500                 505                 510

Ala Val Ser Glu Asn His Ile Leu Glu Asp Val Asn Lys Cys Val Ile
                515                 520                 525

Ala Leu Gln Glu Lys Asp Val Asp Gly Leu Asp Arg Thr Ala Gly Ala
530                 535                 540

Ile Arg Gly Arg Ala Ala Arg Val Ile His Val Val Thr Ser Glu Met
545                 550                 555                 560

Asp Asn Tyr Glu Pro Gly Val Tyr Thr Glu Lys Val Leu Glu Ala Thr
                565                 570                 575

Lys Leu Leu Ser Asn Thr Val Met Pro Arg Phe Thr Glu Gln Val Glu
                580                 585                 590

Ala Ala Val Glu Ala Leu Ser Ser Asp Pro Ala Gln Pro Met Asp Glu
                595                 600                 605

Asn Glu Phe Ile Asp Ala Ser Arg Leu Val Tyr Asp Gly Ile Arg Asp
                610                 615                 620

Ile Arg Lys Ala Val Leu Met Ile Arg Thr Pro Glu Glu Leu Asp Asp
625                 630                 635                 640

Ser Asp Phe Glu Thr Glu Asp Phe Asp Val Arg Ser Arg Thr Ser Val
                645                 650                 655

Gln Thr Glu Asp Asp Gln Leu Ile Ala Gly Gln Ser Ala Arg Ala Ile
                660                 665                 670

Met Ala Gln Leu Pro Gln Glu Gln Lys Ala Lys Ile Ala Glu Gln Val
                675                 680                 685

Ala Ser Phe Gln Glu Glu Lys Ser Lys Leu Asp Ala Glu Val Ser Lys
                690                 695                 700

Trp Asp Asp Ser Gly Asn Asp Ile Ile Val Leu Ala Lys Gln Met Cys
705                 710                 715                 720

Met Ile Met Met Glu Met Thr Asp Phe Thr Arg Gly Lys Gly Pro Leu
                725                 730                 735

Lys Asn Thr Ser Asp Val Ile Ser Ala Ala Lys Lys Ile Ala Glu Ala
                740                 745                 750

Gly Ser Arg Met Asp Lys Leu Gly Arg Thr Ile Ala Asp His Cys Pro
                755                 760                 765

Asp Ser Ala Cys Lys Gln Asp Leu Leu Ala Tyr Leu Gln Arg Ile Ala
                770                 775                 780

Leu Tyr Cys His Gln Leu Asn Ile Cys Ser Lys Val Lys Ala Glu Val
785                 790                 795                 800
```

```
Gln Asn Leu Gly Gly Glu Leu Val Val Ser Gly Val Asp Ser Ala Met
                805                 810                 815

Ser Leu Ile Gln Ala Ala Lys Asn Leu Met Asn Ala Val Val Gln Thr
            820                 825                 830

Val Lys Ala Ser Tyr Val Ala Ser Thr Lys Tyr Gln Lys Ser Gln Gly
        835                 840                 845

Met Ala Ser Leu Asn Leu Pro Ala Val Ser Trp Lys Met Lys Ala Pro
    850                 855                 860

Glu Lys Lys Pro Leu Val Lys Arg Glu Lys Gln Asp Glu Thr Gln Thr
865                 870                 875                 880

Lys Ile Lys Arg Ala Ser Gln Lys Lys His Val Asn Pro Val Gln Ala
            885                 890                 895

Leu Ser Glu Phe Lys Ala Met Asp Ser Ile
        900                 905

<210> SEQ ID NO 5
<211> LENGTH: 953
<212> TYPE: PRT
<213> ORGANISM: Homo sapiens
<220> FEATURE:
<221> NAME/KEY: misc_feature
<222> LOCATION: (1)..(953)
<223> OTHER INFORMATION: Alpha-2 Catenin, Swissprot Accession P26232

<400> SEQUENCE: 5

Met Thr Ser Ala Thr Ser Pro Ile Ile Leu Lys Trp Asp Pro Lys Ser
1               5                   10                  15

Leu Glu Ile Arg Thr Leu Thr Val Glu Arg Leu Leu Glu Pro Leu Val
            20                  25                  30

Thr Gln Val Thr Thr Leu Val Asn Thr Ser Asn Lys Gly Pro Ser Gly
        35                  40                  45

Lys Lys Lys Gly Arg Ser Lys Lys Ala His Val Leu Ala Ala Ser Val
    50                  55                  60

Glu Gln Ala Thr Gln Asn Phe Leu Glu Lys Gly Glu Gln Ile Ala Lys
65                  70                  75                  80

Glu Ser Gln Asp Leu Lys Glu Leu Val Ala Ala Val Glu Asp Val
            85                  90                  95

Arg Lys Gln Gly Glu Thr Met Arg Ile Ala Ser Ser Glu Phe Ala Asp
            100                 105                 110

Asp Pro Cys Ser Ser Val Lys Arg Gly Thr Met Val Arg Ala Ala Arg
        115                 120                 125

Ala Leu Leu Ser Ala Val Thr Arg Leu Leu Ile Leu Ala Asp Met Ala
    130                 135                 140

Asp Val Met Arg Leu Leu Ser His Leu Lys Ile Val Glu Glu Ala Leu
145                 150                 155                 160

Glu Ala Val Lys Asn Ala Thr Asn Glu Gln Asp Leu Ala Asn Arg Phe
                165                 170                 175

Lys Glu Phe Gly Lys Lys Met Val Lys Leu Asn Tyr Val Ala Ala Arg
            180                 185                 190

Arg Gln Gln Glu Leu Lys Asp Pro His Cys Arg Asp Glu Met Ala Ala
        195                 200                 205

Ala Arg Gly Ala Leu Lys Lys Asn Ala Thr Met Leu Tyr Thr Ala Ser
    210                 215                 220

Gln Ala Phe Leu Arg His Pro Asp Val Ala Ala Thr Arg Ala Asn Arg
225                 230                 235                 240
```

-continued

```
Asp Tyr Val Phe Lys Gln Val Gln Glu Ala Ile Ala Gly Ile Ser Asn
            245                 250                 255
Ala Ala Gln Ala Thr Ser Pro Thr Asp Glu Ala Lys Gly His Thr Gly
        260                 265                 270
Ile Gly Glu Leu Ala Ala Ala Leu Asn Glu Phe Asp Asn Lys Ile Ile
    275                 280                 285
Leu Asp Pro Met Thr Phe Ser Glu Ala Arg Phe Arg Pro Ser Leu Glu
290                 295                 300
Glu Arg Leu Glu Ser Ile Ile Ser Gly Ala Ala Leu Met Ala Asp Ser
305                 310                 315                 320
Ser Cys Thr Arg Asp Asp Arg Arg Glu Arg Ile Val Ala Glu Cys Asn
                325                 330                 335
Ala Val Arg Gln Ala Leu Gln Asp Leu Leu Ser Glu Tyr Met Asn Asn
            340                 345                 350
Thr Gly Arg Lys Glu Lys Gly Asp Pro Leu Asn Ile Ala Ile Asp Lys
        355                 360                 365
Met Thr Lys Lys Thr Arg Asp Leu Arg Arg Gln Leu Arg Lys Ala Val
    370                 375                 380
Met Asp His Ile Ser Asp Ser Phe Leu Glu Thr Asn Val Pro Leu Leu
385                 390                 395                 400
Val Leu Ile Glu Ala Ala Lys Ser Gly Asn Glu Lys Glu Val Lys Glu
                405                 410                 415
Tyr Ala Gln Val Phe Arg Glu His Ala Asn Lys Leu Val Glu Val Ala
            420                 425                 430
Asn Leu Ala Cys Ser Ile Ser Asn Asn Glu Glu Gly Val Lys Leu Val
        435                 440                 445
Arg Met Ala Ala Thr Gln Ile Asp Ser Leu Cys Pro Gln Val Ile Asn
    450                 455                 460
Ala Ala Leu Thr Leu Ala Ala Arg Pro Gln Ser Lys Val Ala Gln Asp
465                 470                 475                 480
Asn Met Asp Val Phe Lys Asp Gln Trp Glu Lys Gln Val Arg Val Leu
                485                 490                 495
Thr Glu Ala Val Asp Asp Ile Thr Ser Val Asp Asp Phe Leu Ser Val
            500                 505                 510
Ser Glu Asn His Ile Leu Glu Asp Val Asn Lys Cys Val Ile Ala Leu
        515                 520                 525
Gln Glu Gly Asp Val Asp Thr Leu Asp Arg Thr Ala Gly Ala Ile Arg
    530                 535                 540
Gly Arg Ala Ala Arg Val Ile His Ile Ile Asn Ala Glu Met Glu Asn
545                 550                 555                 560
Tyr Glu Ala Gly Val Tyr Thr Glu Lys Val Leu Glu Ala Thr Lys Leu
                565                 570                 575
Leu Ser Glu Thr Val Met Pro Arg Phe Ala Glu Gln Val Glu Val Ala
            580                 585                 590
Ile Glu Ala Leu Ser Ala Asn Val Pro Gln Pro Phe Glu Glu Asn Glu
        595                 600                 605
Phe Ile Asp Ala Ser Arg Leu Val Tyr Asp Gly Val Arg Asp Ile Arg
    610                 615                 620
Lys Ala Val Leu Met Ile Arg Thr Pro Glu Glu Leu Glu Asp Asp Ser
625                 630                 635                 640
Asp Phe Glu Gln Glu Asp Tyr Asp Val Arg Arg Gly Thr Ser Val Gln
                645                 650                 655
Thr Glu Asp Asp Gln Leu Ile Ala Gly Gln Ser Ala Arg Ala Ile Met
```

```
                    660                 665                 670
Ala Gln Leu Pro Gln Glu Glu Lys Ala Lys Ile Ala Glu Gln Val Glu
            675                 680                 685

Ile Phe His Gln Glu Lys Ser Lys Leu Asp Ala Glu Val Ala Lys Trp
        690                 695                 700

Asp Asp Ser Gly Asn Asp Ile Ile Val Leu Ala Lys Gln Met Cys Met
705                 710                 715                 720

Ile Met Met Glu Met Thr Asp Phe Thr Arg Gly Lys Gly Pro Leu Lys
                725                 730                 735

Asn Thr Ser Asp Val Ile Asn Ala Ala Lys Lys Ile Ala Glu Ala Gly
            740                 745                 750

Ser Arg Met Asp Lys Leu Ala Arg Ala Val Ala Asp Gln Cys Pro Asp
        755                 760                 765

Ser Ala Cys Lys Gln Asp Leu Leu Ala Tyr Leu Gln Arg Ile Ala Leu
    770                 775                 780

Tyr Cys His Gln Leu Asn Ile Cys Ser Lys Val Lys Ala Glu Val Gln
785                 790                 795                 800

Asn Leu Gly Gly Glu Leu Ile Val Ser Gly Thr Gly Val Gln Ser Thr
                805                 810                 815

Phe Thr Thr Phe Tyr Glu Val Asp Cys Asp Val Ile Asp Gly Gly Arg
            820                 825                 830

Ala Ser Gln Leu Ser Thr His Leu Pro Thr Cys Ala Glu Gly Ala Pro
        835                 840                 845

Ile Gly Ser Gly Ser Ser Asp Ser Ser Met Leu Asp Ser Ala Thr Ser
    850                 855                 860

Leu Ile Gln Ala Ala Lys Asn Leu Met Asn Ala Val Val Leu Thr Val
865                 870                 875                 880

Lys Ala Ser Tyr Val Ala Ser Thr Lys Tyr Gln Lys Val Tyr Gly Thr
                885                 890                 895

Ala Ala Val Asn Ser Pro Val Val Ser Trp Lys Met Lys Ala Pro Glu
            900                 905                 910

Lys Lys Pro Leu Val Lys Arg Glu Lys Pro Glu Glu Phe Gln Thr Arg
        915                 920                 925

Val Arg Arg Gly Ser Gln Lys Lys His Ile Ser Pro Val Gln Ala Leu
    930                 935                 940

Ser Glu Phe Lys Ala Met Asp Ser Phe
945                 950

<210> SEQ ID NO 6
<211> LENGTH: 781
<212> TYPE: PRT
<213> ORGANISM: Homo sapiens
<220> FEATURE:
<221> NAME/KEY: misc_feature
<222> LOCATION: (1)..(781)
<223> OTHER INFORMATION: beta-Catenin, Swissprot Accession P35222

<400> SEQUENCE: 6

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60
```

```
Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
        210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
                260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
        290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
        370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480
```

```
Ala Gln Asn Ala Val Arg Leu His Tyr Gly Leu Pro Val Val Lys
            485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
                580                 585                 590

Leu Asn Thr Ile Pro Leu Phe Val Gln Leu Leu Tyr Ser Pro Ile Glu
                595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
            770                 775                 780

<210> SEQ ID NO 7
<211> LENGTH: 585
<212> TYPE: PRT
<213> ORGANISM: Homo sapiens
<220> FEATURE:
<221> NAME/KEY: misc_feature
<222> LOCATION: (1)..(585)
<223> OTHER INFORMATION: Involucrin, Swissprot Accession P07476

<400> SEQUENCE: 7

Met Ser Gln Gln His Thr Leu Pro Val Thr Leu Ser Pro Ala Leu Ser
1               5                   10                  15

Gln Glu Leu Leu Lys Thr Val Pro Pro Val Asn Thr His Gln Glu
                20                  25                  30

Gln Met Lys Gln Pro Thr Pro Leu Pro Pro Pro Cys Gln Lys Val Pro
            35                  40                  45

Val Glu Leu Pro Val Glu Val Pro Ser Lys Gln Glu Glu Lys His Met
```

```
                50                  55                  60
Thr Ala Val Lys Gly Leu Pro Glu Gln Glu Cys Glu Gln Gln Gln Lys
 65                  70                  75                  80

Glu Pro Gln Glu Gln Glu Leu Gln Gln Gln His Trp Glu Gln His Glu
                     85                  90                  95

Glu Tyr Gln Lys Ala Glu Asn Pro Glu Gln Gln Leu Lys Gln Glu Lys
                    100                 105                 110

Thr Gln Arg Asp Gln Gln Leu Asn Lys Gln Leu Glu Glu Lys Lys
                115                 120                 125

Leu Leu Asp Gln Gln Leu Asp Gln Glu Leu Val Lys Arg Asp Glu Gln
                130                 135                 140

Leu Gly Met Lys Lys Glu Gln Leu Leu Glu Leu Pro Glu Gln Gln Glu
145                 150                 155                 160

Gly His Leu Lys His Leu Glu Gln Glu Gly Gln Leu Lys His Pro
                165                 170                 175

Glu Gln Gln Glu Gly Gln Leu Glu Leu Pro Glu Gln Gln Glu Gly Gln
                180                 185                 190

Leu Glu Leu Pro Glu Gln Gln Glu Gly Gln Leu Glu Leu Pro Glu Gln
                195                 200                 205

Gln Glu Gly Gln Leu Glu Leu Pro Glu Gln Gln Glu Gly Gln Leu Glu
                210                 215                 220

Leu Pro Gln Gln Gln Glu Gly Gln Leu Glu Leu Ser Glu Gln Gln Glu
225                 230                 235                 240

Gly Gln Leu Glu Leu Ser Glu Gln Gln Glu Gly Gln Leu Glu Leu Ser
                245                 250                 255

Glu Gln Gln Glu Gly Gln Leu Lys His Leu Glu His Gln Glu Gly Gln
                260                 265                 270

Leu Glu Val Pro Glu Glu Gln Met Gly Gln Leu Lys Tyr Leu Glu Gln
                275                 280                 285

Gln Glu Gly Gln Leu Lys His Leu Asp Gln Glu Lys Gln Pro Glu
                290                 295                 300

Leu Pro Glu Gln Gln Met Gly Gln Leu Lys His Leu Glu Gln Gln Glu
305                 310                 315                 320

Gly Gln Pro Lys His Leu Glu Gln Glu Gly Gln Leu Glu Gln Leu
                325                 330                 335

Glu Glu Gln Glu Gly Gln Leu Lys His Leu Glu Gln Gln Glu Gly Gln
                340                 345                 350

Leu Glu His Leu Glu His Gln Glu Gly Gln Leu Gly Leu Pro Glu Gln
                355                 360                 365

Gln Val Leu Gln Leu Lys Gln Leu Glu Lys Gln Gln Gly Gln Pro Lys
                370                 375                 380

His Leu Glu Glu Glu Glu Gly Gln Leu Lys His Leu Val Gln Gln Glu
385                 390                 395                 400

Gly Gln Leu Lys His Leu Val Gln Gln Glu Gly Gln Leu Glu Gln Gln
                    405                 410                 415

Glu Arg Gln Val Glu His Leu Glu Gln Gln Val Gly Gln Leu Lys His
                420                 425                 430

Leu Glu Glu Gln Glu Gly Gln Leu Lys His Leu Glu Gln Gln Gly
                435                 440                 445

Gln Leu Glu Val Pro Glu Gln Val Gly Gln Pro Lys Asn Leu Glu
                450                 455                 460

Gln Glu Glu Lys Gln Leu Glu Leu Pro Glu Gln Gln Glu Gly Gln Val
465                 470                 475                 480
```

```
Lys His Leu Glu Lys Gln Glu Ala Gln Leu Glu Leu Pro Gln Gln
            485                 490                 495

Val Gly Gln Pro Lys His Leu Glu Gln Glu Lys His Leu Glu His
            500                 505                 510

Pro Glu Gln Gln Asp Gly Leu Lys His Leu Glu Gln Glu Gly
            515                 520                 525

Gln Leu Lys Asp Leu Glu Gln Lys Gly Gln Leu Glu Gln Pro Val
            530                 535                 540

Phe Ala Pro Ala Pro Gly Gln Val Gln Asp Ile Gln Pro Ala Leu Pro
545                 550                 555                 560

Thr Lys Gly Glu Val Leu Leu Pro Val Glu His Gln Gln Lys Gln
            565                 570                 575

Glu Val Gln Trp Pro Pro Lys His Lys
            580                 585

<210> SEQ ID NO 8
<211> LENGTH: 968
<212> TYPE: PRT
<213> ORGANISM: Homo sapiens
<220> FEATURE:
<221> NAME/KEY: misc_feature
<222> LOCATION: (1)..(968)
<223> OTHER INFORMATION: p120, Swissprot Accession O60716

<400> SEQUENCE: 8

Met Asp Asp Ser Glu Val Glu Ser Thr Ala Ser Ile Leu Ala Ser Val
1               5                   10                  15

Lys Glu Gln Glu Ala Gln Phe Glu Lys Leu Thr Arg Ala Leu Glu Glu
            20                  25                  30

Glu Arg Arg His Val Ser Ala Gln Leu Glu Arg Val Arg Val Ser Pro
        35                  40                  45

Gln Asp Ala Asn Pro Leu Met Ala Asn Gly Thr Leu Thr Arg Arg His
    50                  55                  60

Gln Asn Gly Arg Phe Val Gly Asp Ala Asp Leu Glu Arg Gln Lys Phe
65                  70                  75                  80

Ser Asp Leu Lys Leu Asn Gly Pro Gln Asp His Ser His Leu Leu Tyr
                85                  90                  95

Ser Thr Ile Pro Arg Met Gln Glu Pro Gly Gln Ile Val Glu Thr Tyr
            100                 105                 110

Thr Glu Glu Asp Pro Glu Gly Ala Met Ser Val Val Ser Val Glu Thr
        115                 120                 125

Ser Asp Asp Gly Thr Thr Arg Arg Thr Glu Thr Thr Val Lys Lys Val
    130                 135                 140

Val Lys Thr Val Thr Thr Arg Thr Val Gln Pro Val Ala Met Gly Pro
145                 150                 155                 160

Asp Gly Leu Pro Val Asp Ala Ser Ser Val Ser Asn Asn Tyr Ile Gln
                165                 170                 175

Thr Leu Gly Arg Asp Phe Arg Lys Asn Gly Asn Gly Gly Pro Gly Pro
            180                 185                 190

Tyr Val Gly Gln Ala Gly Thr Ala Thr Leu Pro Arg Asn Phe His Tyr
        195                 200                 205

Pro Pro Asp Gly Tyr Ser Arg His Tyr Glu Asp Gly Tyr Pro Gly Gly
    210                 215                 220

Ser Asp Asn Tyr Gly Ser Leu Ser Arg Val Thr Arg Ile Glu Glu Arg
225                 230                 235                 240
```

-continued

```
Tyr Arg Pro Ser Met Glu Gly Tyr Arg Ala Pro Ser Arg Gln Asp Val
            245                 250                 255

Tyr Gly Pro Gln Pro Gln Val Arg Val Gly Gly Ser Ser Val Asp Leu
        260                 265                 270

His Arg Phe His Pro Glu Pro Tyr Gly Leu Glu Asp Asp Gln Arg Ser
    275                 280                 285

Met Gly Tyr Asp Asp Leu Asp Tyr Gly Met Met Ser Asp Tyr Gly Thr
290                 295                 300

Ala Arg Arg Thr Gly Thr Pro Ser Asp Pro Arg Arg Leu Arg Ser
305                 310                 315                 320

Tyr Glu Asp Met Ile Gly Glu Glu Val Pro Ser Asp Gln Tyr Tyr Trp
                325                 330                 335

Ala Pro Leu Ala Gln His Glu Arg Gly Ser Leu Ala Ser Leu Asp Ser
            340                 345                 350

Leu Arg Lys Gly Gly Pro Pro Pro Asn Trp Arg Gln Pro Glu Leu
        355                 360                 365

Pro Glu Val Ile Ala Met Leu Gly Phe Arg Leu Asp Ala Val Lys Ser
    370                 375                 380

Asn Ala Ala Tyr Leu Gln His Leu Cys Tyr Arg Asn Asp Lys Val
385                 390                 395                 400

Lys Thr Asp Val Arg Lys Leu Lys Gly Ile Pro Val Leu Val Gly Leu
                405                 410                 415

Leu Asp His Pro Lys Lys Glu Val His Leu Gly Ala Cys Gly Ala Leu
            420                 425                 430

Lys Asn Ile Ser Phe Gly Arg Asp Gln Asp Asn Lys Ile Ala Ile Lys
        435                 440                 445

Asn Cys Asp Gly Val Pro Ala Leu Val Arg Leu Arg Lys Ala Arg
    450                 455                 460

Asp Met Asp Leu Thr Glu Val Ile Thr Gly Thr Leu Trp Asn Leu Ser
465                 470                 475                 480

Ser His Asp Ser Ile Lys Met Glu Ile Val Asp His Ala Leu His Ala
                485                 490                 495

Leu Thr Asp Glu Val Ile Ile Pro His Ser Gly Trp Glu Arg Glu Pro
            500                 505                 510

Asn Glu Asp Cys Lys Pro Arg His Ile Glu Trp Glu Ser Val Leu Thr
        515                 520                 525

Asn Thr Ala Gly Cys Leu Arg Asn Val Ser Ser Glu Arg Ser Glu Ala
    530                 535                 540

Arg Arg Lys Leu Arg Glu Cys Asp Gly Leu Val Asp Ala Leu Ile Phe
545                 550                 555                 560

Ile Val Gln Ala Glu Ile Gly Gln Lys Asp Ser Asp Ser Lys Leu Val
                565                 570                 575

Glu Asn Cys Val Cys Leu Leu Arg Asn Leu Ser Tyr Gln Val His Arg
            580                 585                 590

Glu Ile Pro Gln Ala Glu Arg Tyr Gln Glu Ala Ala Pro Asn Val Ala
        595                 600                 605

Asn Asn Thr Gly Pro His Ala Ala Ser Cys Phe Gly Ala Lys Lys Gly
    610                 615                 620

Lys Asp Glu Trp Phe Ser Arg Gly Lys Lys Pro Ile Glu Asp Pro Ala
625                 630                 635                 640

Asn Asp Thr Val Asp Phe Pro Lys Arg Thr Ser Pro Ala Arg Gly Tyr
                645                 650                 655

Glu Leu Leu Phe Gln Pro Glu Val Val Arg Ile Tyr Ile Ser Leu Leu
```

-continued

```
                660                 665                 670
Lys Glu Ser Lys Thr Pro Ala Ile Leu Glu Ala Ser Ala Gly Ala Ile
            675                 680                 685

Gln Asn Leu Cys Ala Gly Arg Trp Thr Tyr Gly Arg Tyr Ile Arg Ser
        690                 695                 700

Ala Leu Arg Gln Glu Lys Ala Leu Ser Ala Ile Ala Asp Leu Leu Thr
705                 710                 715                 720

Asn Glu His Glu Arg Val Val Lys Ala Ala Ser Gly Ala Leu Arg Asn
                725                 730                 735

Leu Ala Val Asp Ala Arg Asn Lys Glu Leu Ile Gly Lys His Ala Ile
            740                 745                 750

Pro Asn Leu Val Lys Asn Leu Pro Gly Gly Gln Gln Asn Ser Ser Trp
        755                 760                 765

Asn Phe Ser Glu Asp Thr Val Ile Ser Ile Leu Asn Thr Ile Asn Glu
        770                 775                 780

Val Ile Ala Glu Asn Leu Glu Ala Ala Lys Lys Leu Arg Glu Thr Gln
785                 790                 795                 800

Gly Ile Glu Lys Leu Val Leu Ile Asn Lys Ser Gly Asn Arg Ser Glu
                805                 810                 815

Lys Glu Val Arg Ala Ala Ala Leu Val Leu Gln Thr Ile Trp Gly Tyr
            820                 825                 830

Lys Glu Leu Arg Lys Pro Leu Glu Lys Glu Gly Trp Lys Lys Ser Asp
        835                 840                 845

Phe Gln Val Asn Leu Asn Asn Ala Ser Arg Ser Gln Ser Ser His Ser
        850                 855                 860

Tyr Asp Asp Ser Thr Leu Pro Leu Ile Asp Arg Asn Gln Lys Ser Asp
865                 870                 875                 880

Lys Lys Pro Asp Arg Glu Glu Ile Gln Met Ser Asn Met Gly Ser Asn
                885                 890                 895

Thr Lys Ser Leu Asp Asn Asn Tyr Ser Thr Pro Asn Glu Arg Gly Asp
            900                 905                 910

His Asn Arg Thr Leu Asp Arg Ser Gly Asp Leu Gly Asp Met Glu Pro
        915                 920                 925

Leu Lys Gly Thr Thr Pro Leu Met Gln Asp Glu Gly Gln Glu Ser Leu
        930                 935                 940

Glu Glu Glu Leu Asp Val Leu Val Leu Asp Asp Glu Gly Gly Gln Val
945                 950                 955                 960

Ser Tyr Pro Ser Met Gln Lys Ile
                965
```

METHOD FOR SOLUTION BASED DIAGNOSIS

This application claims benefit to a foreign application, EP 02017313.4, filed Aug. 1, 2002.

FIELD OF THE INVENTION

This invention relates to methods for performing diagnosis of medically relevant conditions by detecting the levels of relevant markers characteristic for the medically relevant condition and the levels of normalization markers. The methods pertain to characterization of the sample in a solution phase, without relying on morphological cell based information.

BACKGROUND OF THE INVENTION

The diagnosis of a large number of medically relevant conditions is currently performed using molecular markers as tools. The molecular tools are generally used as one aspect in a complex examination, taking into account a series of different parameters characterizing the samples to be examined.

In medically relevant analysis, the morphological examination of samples by cytological or histological means is in common use. Such methods based on morphological characterization of cell based samples are applicable for example in analysis of clinical samples such as body fluids, blood, surgical resections, secretions, swabs or lavages.

In screening for cervical cancer, for example, swabs are used for detection of neoplastic lesions of the cervix uteri. In the screening procedure, lesions of different origin have to be distinguished. Causes for lesions may for example be inflammations (due to infectious agents or physical or chemical damage) or preneoplastic and neoplastic changes. In morphological examinations the lesions of different characteristics are sophisticated to distinguish. Thus, for examination of swabs, cytologists and pathologists have to be especially trained and even experienced examiners have a high inter- and intra-observer variance in the assessment of a diagnosis based on cytological specimens. In general the result of the examination is based upon the subjective interpretation of diagnostic criteria by the examining pathologist/cytologist. As a result the rate of false positive and false negative results in the screening tests remains unsatisfying high.

Therefore, in many cases these cytological or histological examination procedures are supported by the use of molecular markers. Such markers are often used in immuno-histochemical staining reactions, or in the course of in-situ hybridization reactions. In the prior art combinations of morphological examinations and immuno-histochemical staining reactions based on marker molecules, characteristic for different medically relevant states of tissues or cells, may lead to enhanced results. The morphologic examination remains laborious and time consuming and thus expensive, even when supported by the molecular methods, that make the results more reliable. Additionally, the diagnosis on a morphologically cell based level is, even when supported by molecular parameters, subject to individual perception of the morphology by individual examiners. Thus the diagnosis is dependent on the person, that performs the examinations.

Only in very few cases, molecular markers may be used as diagnostic tools without further support by cell based morphological examinations. This is especially the case, if markers are to be detected in an environment, where they do only occur under exactly defined conditions. So the methods for diagnosis of conditions on a molecular level only, without the support of cell based information, are restricted to cases, where there are suitable markers, that are non-ambiguously specific for the condition to be characterized. For example, detection of viral infections may be carried out in solutions of samples, because the markers characteristic for the presence of viruses in tissues do not occur in unaffected human tissues.

The reproducibility of the results of examination can be enhanced by the use of supporting molecular tools. However, the problem with the preservation and preparation of the samples may not be overcome by just additionally using molecular markers.

When using molecular tools in cytological or histological examinations, strict precautions in preserving the samples have to be taken to prevent artefacts and improper results of the tests. This is in part due to the instability of the cell based morphological information and in part to the instability of the molecular markers to be detected during the tests. If the samples are not prepared, transported or stored in the appropriate manner, the cell based information, or even the molecular information may get lost, or may be altered. So the diagnosis may be impossible, or may be prone to artefacts. For example, the interpretation of biopsies or cytological preparations is frequently made difficult or impossible because of damaged (physically or biochemically) cells. Regarding tissue samples or biopsies, the preservation of molecular constituents of the samples, which are subject to a rapid turnover, seems sophisticated due to the time elapsed until penetration of the total sample by appropriate preservatives.

The morphologically supported diagnostic methods performed routinely in the art show two major disadvantages. First, the methods are highly dependent on individual perception of the examiners. Secondly the morphological information is quite sensitive to decay processes and thus may cause artefacts after preparation of the samples. Both aspects contribute to improper reproducibility of the results.

For improved diagnosis of medically relevant conditions, methods that do not depend on cell based morphological information would be desirable.

SUMMARY OF THE INVENTION

The present invention is directed to a method for diagnosing a medically relevant condition of a patient. The method comprises the steps of: obtaining a raw sample containing cells or cell debris from a patient; preparing a sample solution from the raw sample; detecting the levels of one or more relevant markers characteristic for said medically relevant condition in said sample solution; detecting the levels of one or more normalization markers; normalizing the detected level of the relevant markers with respect to said normalization parameters; and diagnosing the medically relevant condition from the normalized levels of said relevant markers within the sample solution. The normalization markers are characteristic for at least one of the following normalization parameters: the presence or absence of a particular cell type among the cells represented within the sample solution, the presence or absence of a particular differentiation pattern in the cells represented within the sample solution, and the presence or absence of particular proliferation properties of the cells represented within the sample solution.

In one embodiment of the invention, the medically relevant condition is a cell proliferative disorder, cancer or a precursory lesion.

The present invention is also directed to a test kit for diagnosing a medically relevant condition.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

FIG. 1A shows a positive reaction detected in columnar epithelium of the endocervix using an antibody directed against cytokeratin 18 (CK18). FIG. 1B shows no specific staining in columnar epithelium of the ectocervix using an antibody directed against cytokeratin 18 (CK18). FIG. 1C shows no specific staining in columnar epithelium of the endocervix using an antibody directed against cytokeratin 10/13 (CK10/13). FIG. 1D shows a strong staining of the squamous epithelium of the ectocervix using an antibody directed against cytokeratin 10/13 (CK10/13).

DETAILED DESCRIPTION OF THE INVENTION

Figure 1:
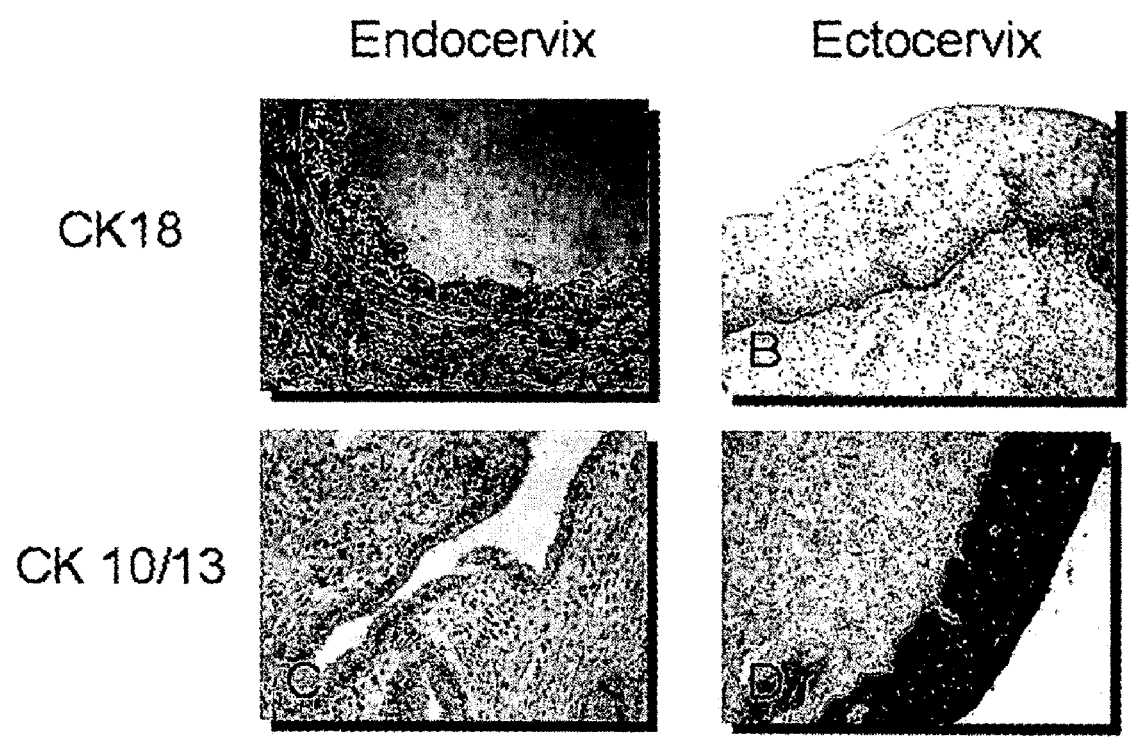
FIG. 1 shows the specific immunohistochemical staining of endocervical and ectocervical epithelial cells in cervical sections.

This invention provides methods for improved diagnosis of medically relevant conditions by solution-based biochemical testing procedures performed in solutions of test samples. The invention provides a method to substitute the cell based morphological information contained within the cytological and/or histological data of the test sample by molecular information obtainable from the solution, wherein the original test sample is dissolved and thus enables for accurate and reproducible assessment of medically relevant diagnosis from dissolved test samples. The method according to the invention comprises the steps of determining the levels of one or more markers associated with the condition to be diagnosed, determining the level of a set of normalization markers suitable to substitute the information related to morphological aspects of the sample, that would have enabled or supported diagnosis in a cell based test system, comparing and/or combining the data concerning the levels of said markers and assessing diagnosis of a medically relevant condition.

The present invention discovers that diagnosis of conditions, which is normally (in cell based diagnostic systems) enabled and/or supported by histological and/or cytological examination procedures, may be performed in solutions from raw samples containing various cell types of different characteristics, by a method comprising the steps of obtaining a raw sample, dissolving the sample in an appropriate solute, detecting the level of one or more markers associated with the condition to be diagnosed and additionally one or more normalization markers within the sample solution, normalizing the data correlating to the markers associated with said condition with respect to the data correlating to the normalization markers and diagnosing the presence or absence of a condition in the sample.

The method according to the present invention may for example be applied as a primary screening test in cases, where a cytological, histological or pathological examination is normally performed. Using the present invention one may discriminate, if the condition to be diagnosed may be present in the sample. If the solution based diagnosis gives a negative result concerning a particular condition, a further examination may be omissible. In case of positive results, ascertaining by classically applicable methods may follow. Thus, expensive and time consuming microscopic or other examinations could be avoided by means of an inexpensive rapid primary screening test.

One aspect of the present invention is a method for enhanced diagnosis of medically relevant conditions, wherein the assessment of diagnosis is performed using solutions of lysed raw tissue- or cell-samples. The method for diagnosis disclosed according to the present invention does not rely on morphological parameters but enables for a diagnosis by means of biochemical analysis.

A second aspect of the present invention is a method for characterizing a complex sample in solution by means of molecular markers characteristic for the parameters of interest, thus substituting information, which could otherwise be obtainable from cytological or histological examinations.

A third aspect of the present invention is to provide suitable combinations of markers for the diagnosis of particular conditions of medical relevance in complex samples. The markers for normalization are chosen such that parameters included within the raw sample, that enable or support the diagnosis, which are lost by the dissolution of the sample, may be substituted.

A fourth aspect of the present invention are test kits for performing diagnostic or research studies according to the present invention.

The present invention enables for a rapid and easy assay for diagnosing of conditions in raw samples such as body fluids, swabs, lavages (e.g. bronchio-alveolar ravages, breast ductal lavages, etc.), aspirates (needle-aspirates, fine-needle-aspirates) or complex cell- or tissue samples. In general, a problem with raw materials is the presence of a number of different cell-types within the sample and the presence of particular microorganisms and extracellular substances. Thus the raw material contains a mixture of cells and compositions, that is prone to give artefacts as results. The presence of different cell types with different proliferative characteristics, of organisms and substances within the raw sample gives rise to multiple factors, that may contribute to the particular level of a marker molecule. Detecting solely the level of one single molecular marker may thus only lead to a diagnostically useful information, if further (morphological) parameters concerning the raw sample are provided. All morphologic data obtainable from the raw sample are lost due to lysis in solution. Yet there are suitable molecular markers corresponding to particular morphologic or other parameters obtainable by histological, cytological methods.

For example, the information about the single constituents within the raw sample may be classically obtained by microscopic examination. Morphologic inspection gives hints about the differentiation, the localization of cells, as well as about the environment, in which the cells appear. In cytological preparations of cervical-swabs, for example, the particular cells may be identified as epithelial cells and further categorized as e.g. endocervical or ectocervical epithelial cells. Even the presence of non-cervical cells such as endometrial cells may be ascertained easily by microscopic inspection.

According to the present invention, raw materials may directly be dissolved in an appropriate solvent without further preparation or characterization independent of the homogeneous or heterogeneous character of the sample material. Data, which are lost through lysis of the material are contained within the sample solution encoded by the levels of a series of marker molecules and may thus be reconstructed using said molecular data for normalization to the respective morphologic characteristics. This is achieved by employing a suitable set of molecular markers for each of the characteristic parameters needed for unambiguous diagnosis. By detecting a suitable array of markers one may assess the relevant parameters characterizing the raw sample and thus overcome the disadvantage of loss of information through lysis of the sample.

The testing procedure according to the present invention includes detecting the levels of markers characteristic for cell conditions in question and of markers for normalizing the data with respect to parameters characterizing the particular environment in the test sample. The markers suitable for the present invention may be of various origin. The expression pattern of a marker, that is suitable for the detection of conditions in question, may be dependent on the proliferative status of cells, on the differentiation status, on the cell type or on the organism. Examples for appropriate markers are set forth below.

The term diagnosis as used herein generally comprises any kind of assessment of the presence of absence of a medically relevant condition. Diagnosis thus comprises processes such as screening for the predisposition for a medically relevant condition, screening for the precursor of a medically relevant condition, screening for a medically relevant condition, clinical or pathological diagnosis of a medically relevant condition, etc. Diagnosis of medically relevant conditions as used herein may comprise examination of any condition, that is detectable on a cytological, histological, biochemical or molecular biological level, that may be useful in respect to the human health and/or body. Such examinations may comprise e.g. medically diagnostic methods and research studies in life sciences. In one embodiment of the invention, the method is used for diagnosis of medically relevant conditions such as e.g. diseases. Such diseases may for example comprise disorders characterized by non-wild type proliferation of cells or tissues.

In one embodiment, the diagnosis pertains to diagnosis of cancers and their precursory stages, to monitoring of the disease course in cancers, to assessment of prognosis in cancers and to detection of disseminated tumor cells e.g. in the course of minimal residual disease diagnosis. The method according to the present invention may for example be used in the course of clinical or pathological diagnosis of cancers and their precursory stages or in routine screening tests as performed for particular cancers such as for example for examination of swabs e.g. in screening tests for cervical lesions, of bronchial lavages for lung cancer or of stool for lesions of the gastrointestinal tract, e.g. colorectal lesions.

The method according to the present invention is applicable to all kinds of medically relevant conditions.

Medically relevant conditions as used according to the present invention may for example be compositions of tissues, body fluids, secretions, washes or swabs. Such conditions may for example comprise the cellular composition of body fluids, such as the composition of blood, the composition of liquor or the composition of semen. In this context the compositions shall be for example the presence or absence of particular cell types (e.g. pathogens, such as, viruses etc., preneoplastic, neoplastic and/or dysplastic cells etc.), the presence or absence of differentiation patterns of particular cell types, the total number of a particular cell types (e.g. erythrocytes, leucocytes, sperm, etc.), the total number of all cells of any cell types or the fraction of cells of particular other characteristics present or absent in the sample.

Furthermore, medically relevant conditions may also comprise disorders related to cells, or tissues. The conditions to be diagnosed may comprise parameters related to cells in cytological or histological tissue samples. The conditions may comprise a differentiation pattern of cells in a tissue sample, such as surgical resection samples, biopsies, swabs, lavages etc. Such conditions may comprise e.g. congenital disorders, inflammatory disorders, mechanical disorders, traumatic disorders, vascular disorders, degenerative disorders, growth disorders, benign neoplasms, malignant neoplasms. Another aspect of the conditions according to the present invention may comprise conditions characterized by the presence or absence of proliferative characteristics. Conditions characterized by the presence or absence of proliferative characteristics may be for example cell proliferative disorders.

Cell proliferative disorders according to the present invention comprise diseases characterized by abnormal growth properties of cells or tissues compared to the growth properties of normal control cells or tissues. The growth of the cells or tissues may be for example abnormally accelerated, decelerated or may be regulated abnormally. Abnormal regulation as used above may comprise any form of presence or absence of non wild-type responses of the cells or tissues to naturally occurring growth regulating influences. The abnormalities in growth of the cells or tissues may be for example neoplastic or hyperplastic.

In one embodiment, the cell proliferative disorders are tumors. Tumors may comprise tumors of the head and the neck, tumors of the respiratory tract, tumors of the anogenital tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, etc. Tumors may comprise for example neoplasms such as benign and malignant tumors, carcinomas, sarcomas, leukemias, lymphomas or dysplasias. In a particular embodiment, the tumor is for example cancer of the head and the neck, cancer of the respiratory tract, cancer of the anogenital tract, cancer of the gastrointestinal tract, cancer of the skin and its appendages, cancer of the central and peripheral nervous system, cancer of the urinary system, cancer of the reproductive system, cancer of the endocrine system, cancer of the soft tissues and bone, cancer of the hematopoietic and lymphopoietic system.

Tumors of the anogenital tract may comprise cancer of the perineal, the perinanal and the scrotal skin, cervical cancer, cancer of the vulva, cancer of the vagina, caner of the penis, cancer of the anus, etc. Cervical cancer may comprise squamous lesions, glandular lesions or other epithelial tumors. Squamous lesions comprise, e.g., cervical intraepithelial neoplasias (mild, moderate and severe dysplasia), carcinoma in-situ, squamous cell carcinoma (e.g., keratinizing, nonkeratinizing, verrucous, warty, papillary, lymphoepithelioma-like). Glandular lesions may comprise atypical hyperplasias, adenocarcinoma in-situ, andenocarcinoma (such as, e.g., mucinous, endometrioid, clear cell, adenoma malignum, papillary, serous or mesonephric adenocarcinoma). Other epithelial tumors may comprise adenosquamous carcinoma, glassy cell carcinoma, adenoid cystic carcinoma, adenoid basal carcinoma, carcinoid tumor, small cell carcinoma and undifferentiated carcinoma. For more detailed information, confer "Kurman, R., Norris, H., et al., *Tumors of the Cervix, Vagina, and Vulva, Atlas of Tumor Pathology*, 1992, AFIP," the contents of which shall be incorporated herein by reference.

Gastrointestinal tumors may comprise colon cancer, cancer of the colon ascendens, of the colon descendens, of the colon transversum, of the sigmoidum, of the rectum, cancer of the small intestine, cancer of the jejunum, cancer of the duodenum, gastric cancer, oesophageal cancer, liver cancer, cancer of the bile, cancer of the biliary system, pancreatic cancer, etc. A comprehensive overview over gastrointestinal lesions is given in "Hamilton Sr, Aaltonen L A (Eds.): World Health Organization Classification of Tumours, *Pathology and Genetics of Tumors of the Digestive System*, IARC Press: Lyon 2000," which shall be incorporated herein by reference.

Tumors of the respiratory tract may comprise any malignant condition of the respiratory tract such as, e.g., cancer of the lung, the alveoles, the bronchioles, the bronchial tree and the broncus, the nasopharyngeal space, the oral cavity, the pharynx, the nasal cavity and the paranasal sinus. Lung cancer such as small cell lung cancer, non-small cell lung cancer, squamous cell lung carcinoma, small cell lung carcinoma, adenocarcinoma of the lung, large cell lung carcinoma, adeno-squamous lung carcinoma, carcinoid tumor of the lung, broncheal gland tumor or (malignant) mesothelioma. An overview over tumors of the respiratory tract may be found in Colby TV, et al.: *Tumors of the Lower Respiratory Tract*, Atlas of Tumor Pathology, Third Series, Fascicle 13, AFIP: Washington 1995," which shall be incorporated herein by reference.

Tumors of the urinary system may comprise bladder cancer, cancer of the kidney, renal pelvis, cancer of the ureters and cancer of the urethra, etc. Tumors of the reproductive system may comprise cancer and precursor stages thereof of the ovary, the uterus, the testis, the prostate, the epididymis, etc.

In all cases, the methods according to the present invention also apply to precursor stages of the lesions, tumors or cancers.

In one embodiment, the method according to the present invention pertains to the detection of disseminated tumor cells or metastases.

In one embodiment of the invention, the carcinoma is e.g. cervical cancer, colon cancer, gastric cancer, breast cancer, bladder cancer, lung cancer, cancer of the oral cavity etc.

The present invention provides a number of robust, fast and easy ways to preserve molecular properties of samples, whereby the morphological information of samples is lost. Samples may be e.g. prepared in a reproducible and easy to store and transport form by dissolving the cellular components of the raw sample in a suitable solvent immediately after or even during obtaining the sample. Body fluids may directly be transferred from the body of an individual to a solution containing suitable detergents and preservative substances. Furthermore, tissue samples may immediately be transferred to denaturing lysis conditions (eventually supported by physical forces) and be thus preserved. Using appropriate ingredients in the solvent, the molecular components of the original sample may be preserved, and no degradation may occur. The degradation by enzymatic activities may, for example, be minimized by the use of enzyme inhibitors. Thus, a solution of test samples may easily represent the molecular properties of a test sample at the time of dissolution, without requiring additional preservative precautions.

Raw samples may comprise clinical samples, such as e.g. secretions, swabs, lavages, body fluids, blood, urine, semen, stool, bile, liquor, bone marrow, biopsies, cell- and tissue-samples. Biopsies as used in the context of the present invention may comprise e.g. resection samples of tumors, tissue samples prepared by endoscopic means or punch- or needle-biopsies of organs. Furthermore, any sample potentially containing the marker molecules to be detected may be a sample according to the present invention. In one embodiment of the invention, the sample comprises cervical swabs, bronchial lavages, stool etc. Raw sample as used in the context of the present invention may comprise fixed or preserved cell or tissue samples. E.g. cells preserved in suitable solutions (alcohols etc.) or fixed tissue samples may be used as raw samples in the methods according to the present invention.

A raw sample according to the method of the present invention includes any sample comprising cells or cell debris. The cells may for example be prokaryotic or eukaryotic cells. When the present invention is applied for the detection of infectious diseases, the cells to be determined may be cells of microorganisms such as *chlamydia, E. coli, candida*, etc.

According to the present invention, all or part of the molecular components of the raw samples are solubilized in a suitable lysis buffer comprising e.g. solvents. Such solvents may for example be aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), non-ionic detergents (e.g. TWEEN 20, Nonidet P-40, TRITON X-100, NP-40, IGEPAL CA-630, N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH. The solvent is designed, so that cells, cell debris, nucleic acids, polypeptides, lipids and other biomolecules potentially present in the raw sample are dissolved. The solution for dissolving the raw samples according to the present invention may furthermore comprise one or more agents that prevent the degradation of components within the raw samples. Such components may for example comprise enzyme inhibitors such as proteinase inhibitors, RNAse inhibitors, DNAse inhibitors etc. In one embodiment of the present invention the sample is lysed directly in the form it is obtainable from the test-individuals. In another embodiment of the present invention the sample may be further purified before being lysed. Such purification procedures may for example comprise washing away of contaminants such as mucus or the like, separation or concentration of cellular components, preserving and transporting of the cells. Thus the cellular components of the raw samples are included in a single sample solution.

The preparation of a sample for use in a method as disclosed herein may also comprise several steps of further preparations of the sample, such as separation of insoluble components, isolation of polypeptides or nucleic acids, preparation of solid phase fixed peptides or nucleic acids or preparation of beads, membranes or slides to which the molecules to be determined are coupled covalently or non-covalently.

According to the present invention, all or part of the molecular components of the raw samples are solubilized in a suitable lysis buffer comprising e.g. solvents. Such solvents may for example be aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), non-ionic detergents (e.g. TWEEN®-20, polyethylene glycol sorbitan monolaurate; nonidet P-40, TRITON® X-100, t-octylphenoxypolyethoxyethanol; NP-40, IGEPAL® CA-630, nonidet P 40; N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH. The solvent is designed, so that cells, cell debris, nucleic acids, polypeptides, lipids and other biomolecules potentially present in the raw sample are dissolved. The solution for dissolving the raw samples according to the present invention may furthermore comprise one or more agents that prevent the degradation of components within the raw samples. Such components may for example comprise enzyme inhibitors such as proteinase inhibitors, RNAse inhibitors, DNAse inhibitors etc. In one embodiment of the present invention the sample is lysed directly in the form it is obtainable from the test-individuals. In another embodiment of the present invention the sample may be further purified before being lysed. Such purification procedures may for example comprise washing away of contaminants such as mucus or the like, separation or concentration of cellular components, preserving and transporting of the cells. Thus the cellular components of the raw samples are included in a single sample solution.

The terms "marker" or "marker molecule" in all their grammatical forms as used in the context of the present invention refers to nucleic acid as well as polypeptide molecules. Marker or marker molecule thus comprises e.g. RNA (MRNA, hnRNA, etc.), DNA (cDNA, genomic DNA, etc.), proteins, polypeptides, proteoglycans, glycoproteins and the respective fragments of these molecules. The term "relevant marker" shall refer to marker molecules characteristic for a medically relevant condition. The term normalization marker shall refer to marker molecules used for normalization purposes.

A level of a marker molecule as used herein refers to a semiquantitave as well as a quantitative value regarding the amount of the respective marker present in a sample. A quantitative value may e.g. be represented in terms of a concentration. A semiquantitative value may be expressed in terms of a scale of levels e.g. undetectable levels, low levels, intermediate levels, high levels or any other suitable mode. The level of a marker may also be represented in terms of a dependent parameter such as the intensity of a signal generated in an assay format in response to the presence of a marker molecule.

A probe for the detection of the marker molecules as used in the context of the present invention shall be any molecule, that specifically binds to said marker molecules. The probe may for example be an antigen binding agent such as antibodies (monoclonal or polyclonal), antibody fragments or artificial molecules comprising antigen binding epitopes, DNA or RNA binding molecules such as proteins or nucleic acids. Nucleic acids binding to other nucleic acids may for example be peptide nucleic acids (PNAs) or oligonucleotides (RNA, DNA, PNA, artificial nucleic acids, etc.) for detection purposes or primers.

A molecule is said to recognize another molecules if it specifically interacts with that molecule. Specific interaction may for example be specific binding to or of the other molecule.

The reporter reaction may be for example a reaction producing a colored compound. In one embodiment of the present invention the reporter substances correlated to the particular markers develop different colors. In another embodiment, the normalization marker specific reporter may be a molecule quenching the signal produced by the reporter molecule specific for the marker, characteristic for the medically relevant condition, in dependence on the level of the normalization marker present in the sample. In yet another embodiment the reporter reactions may produce fluorescent dyes with differing wavelength characteristics. In a further embodiment of the present invention the reporter reaction may comprise light emitting reactions with different wavelength characteristics for the reporter substances specific for either marker to be detected. In another embodiment of the present invention the reporter reaction may comprise the emission of radioactive radiation and additional methods for visualizing or quantifying the radiation. In one embodiment, the different marker molecules may be recognized by agents, that bear radio-nuclides emitting radiation with different energetic properties, so that the signals referring to marker molecules could be distinguished.

Applicable formats for the detection reaction according to the present invention may be blotting techniques, such as Western-Blot, Southern-blot, Northern-blot. The blotting techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as EIA, ELISA, RIA, lateral flow assays, flow through assays, immunochromatographic strips, etc. Immunoassays for use in the invention may comprise competitive as well as non-competitive immunoassays such as sandwich assays.

In certain embodiments of the invention immunochemical or nucleic acid based testing may be performed using a testing device for clinical laboratories. Such testing device may comprise any device suitable for immunochemical or nucleic acid based testing including any format such as e.g. Point of care testing devices as well as bench top or laboratory devices. The devices may be e.g. provided as open or closed platform systems. The system may be based on any suitable methodology such as e.g. employing microtiter plates, multiwell plates, flow through or lateral flow systems, microchip or array based systems or bead or membrane based systems. The detection methods employed may comprise any methods known to those of skill in the art useful for immunochemical or nucleic acids based detection reactions. Such detection systems may be e.g. luminescence systems (electroluminescence, bioluminescence, photoluminescence, radioluminescence, chemiluminescence, electrochemoluminescence), fluorescence based systems, conductivity based detection systems, radiation (light, UV, X-ray, gamma etc.) or any other known method.

The method for detection of the level of the marker molecules in one embodiment of the present invention is any method, which is suited to detect even very small amounts of specific molecules in biological samples. Furthermore any method for detection of the marker molecules irrespective of the sensitivity may be applied. The detection reaction according to the present invention may comprise for example detection reactions on the level of nucleic acids and/or detection reactions on the level of polypeptides. In one embodiment of the invention, the detection of the marker molecules may comprise the detection of particular splicing variants. In another embodiment of the present invention, the detection method may comprise the detection of modifications of marker molecules such as phosphorylation or glycosylation etc of polypeptides or the methylation of nucleic acid molecules in samples.

In one embodiment of the invention, the detection of the level of marker molecules is carried out by detection of the level of nucleic acids coding for the marker molecules or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids. This method can be performed as well in vitro as directly in-situ for example in the course of a detecting staining reaction. Another way of detecting the marker molecules in a sample on the level of nucleic acids performed in the method according to the present invention is an amplification reaction of nucleic acids, which can be carried out in a quantitative manner such as for example the polymerase chain reaction. In one embodiment of the present invention e.g. real time RT PCR may be used to quantify the level of marker RNA in samples of cell proliferative disorders.

In another embodiment of the invention, the detection of the level of marker molecules is carried out by determining the level of expression of a protein. The determination of the marker molecules on the protein level may for example be carried out in a reaction comprising a binding agent specific for the detection of the marker molecules. These binding agents may comprise for example antibodies and antigen-binding fragments, bifunctional hybrid antibodies, peptidomimetics containing minimal antigen-binding epitopes etc. The binding agents may be used in many different detection techniques for example in western-blot, ELISA, RIA, EIA, flow through assay, lateral flow assay, latex-agglutination, immunochromatographic strips or immuno-precipitation. Generally binding agent based detection may be carried out as well in vitro as directly in situ for example in the course of an immunocytochemical staining reaction. Any other method suitable for determining the amount of particular polypeptides in solutions of biological samples can be used according to the present invention.

Methods for the detection of the modified states of nucleic acid molecules and/or polypeptides are known to those of ordinary skill in the art.

Methods for detection of methylation of nucleic acids are known to those of skill in the art and may comprise for example methods employing chemical pre-treatment of nucleic acids with e.g. sodium bisulphite, permanganate or hydrazine, and subsequent detection of the modification by means of specific restriction endonucleases or by means of specific probes e.g. in the course of an amplification reaction. The detection of methylation may furthermore be performed using methylation specific restriction endonucleases. Methods for the detection of methylation states in nucleic acids are e.g. disclosed in patent application EP02010272.9, U.S. Pat. No. 5,856,094, WO0031294, U.S. Pat. No. 6,331,393 etc. The cited documents are incorporated herein by reference.

Detection of modified states of polypeptides may for example comprise binding agents specifically recognizing modified or unmodified states of polypeptides. Alternatively enzymes such as phosphatases or glycosylases may be used to remove modifications in molecules. The presence or absence of modifications can thus be detected by determination of mass or charge of the molecules by means of electrophoresis, chromatography, mass spectrometry etc. prior and subsequent to the incubation with a respective enzyme.

In a further embodiment of the present invention, the detection of a series of marker molecules is carried out on the level of polypeptides and simultaneously the detection of a further series of marker molecules and/or of all or some of the same marker molecules is carried out on the level of nucleic acids.

Markers associated with medically relevant cellular conditions may e.g. be molecules which influence and/or reflect the proliferation and/or differentiation characteristics of cells and/or tissues. Such molecules may comprise for example cell cycle regulatory proteins, proteins associated with the DNA replication, transmembrane proteins, receptor proteins, signal transducing proteins, calcium binding proteins, proteins containing DNA-binding domains, metalloproteinases, kinases, kinase inhibitors, chaperones, embryogenesis proteins, heat shock proteins or enzymes which modify other proteins posttranslationally thus regulating their activity, or nucleic acids coding for the named proteins. Also mRNA coding for the named proteins may be marker molecules useful according to the present invention. In one embodiment the marker associated with the cell proliferative disorder may be for example uniquely expressed in cells affected by the disorder, may be not expressed in said cells or may be over-expressed in said cells.

Marker molecules for use according to the present invention may comprise one or more markers chosen from p13.5, p14, p15, p16 (also referred to p16$^{INK4a}$), p19, p21, p27, p53, pRb, p14ARF, cyclin A, cyclin B, cyclin E, MDM-2, MCM2, MCM5, MCM6, CDC2, CDC6, Id1, osteopontine, GRP, renal dipeptidase, her2/neu, TGFβII receptor, HPV associated markers e.g. derived from HPV genes L1, L2, E1, E2, E4, E5, E6 or E7, etc. A selection of markers useful in one embodiment of the present invention for the detection of medically relevant conditions is shown below in Table 1.

In one embodiment the marker for a medically relevant condition may be a marker for tumors (tumor markers). The marker molecules characteristic for tumors may e.g. be proteins, that are expressed in a non-wild type manner in tumors compared to normal control tissue. Non-wild type expression as used herein may comprise increased or decreased levels of expression or lack of expression or expression of non-wild type forms of the respective molecules. Expression of non-wild type forms of a protein may comprise expression of mutated forms of proteins, arising by insertion, deletion, substitution, or frameshift mutations or any other known types of mutations in proteins or nucleic acids. In all cases of the expression of non-wild type proteins or non-wild type levels of proteins the proteins, polypeptides or fragments thereof or nucleic acids encoding these proteins or polypeptides or fragments of these nucleic acids may be used as molecular markers associated with tumors and may thus be understood under the term "tumor marker" as used in the context of the present invention. Proteins that show non-wild type expression in association with tumors are disclosed for example in the documents WO9904265A2, WO0149716A2, WO0055633A2 and WO042792A2, which shall be incorporated by reference herein.

In one embodiment of the invention, the marker characteristic for the medically relevant condition may be a cell cycle regulatory protein such as for example a cyclin, a cyclin dependent kinase or a cyclin dependent kinase inhibitor. In a further embodiment of the invention the marker characteristic for the medically relevant condition may be a marker associated with a transient or a persistent viral infection. The viral infection may comprise an infection by a human papilloma virus (HPV) such as high risk or low risk HPV. The high risk HPV may comprise HPV subtypes such as e.g. HPV 16, 18, 31, 33, 35, 39, 45, 51, 52, 56 and 58. The markers for HPV infection may e.g. comprise HPV expression products of HPV genes L1, L2, E2, E4, E5, E6 or E7. In a third embodiment of the invention a marker characteristic for a viral infection may be used in combination with any other marker for a medically relevant condition such as e.g. in combination with a cell cycle regulatory protein. Combinations of marker molecules, which may be of special interest with respect to HPV association are e.g. disclosed in WO0208764 which document shall be incorporated herein by reference.

In one embodiment, cell cycle regulatory proteins for use in combination with HPV markers may for example be chosen from a group comprising pRb, p53, p14 ARF, cyclin dependent kinase inhibitors. In one special embodiment for example p16$^{INK4a}$ may be used in combination with markers for HPV infection (e.g. L1, L2, E2, E4, E5, E6 or E7).

It must be understood, that as the case may be markers useful as markers for medically relevant conditions in certain embodiments may serve as markers for normalization in certain other embodiments and vice versa. However, in each single embodiment, a marker can only serve either as marker for the medically relevant condition or as marker for normalization. For example, Ki67 as a marker for cell proliferation may be useful as a normalization marker in certain embodiments (e.g. in combination with p16, p14ARF, claudin-1 or others as markers for medically relevant condition). In other embodiments, Ki67 may serve as a marker for medically relevant condition (e.g. as a marker for cervical dysplasia or other dysplastic diseases) in combination with suitable normalization markers (e.g. cytokeratins, catenins or others). Various other markers may likewise serve either as a marker for medically relevant conditions or for a normalization depending on the particular embodiment of application.

Normalization markers according to the present invention may comprise for example housekeeping genes, such as actin, gapdh, histone proteins, phospholipase, β2-microglobulin, proteins associated with active cell proliferation such as e.g. Ki67, PCNA or statin, or proteins characteristic for particular cell types such as for example CK20 in epithelial cells or any cell specific cell-surface antigens. In addition, carbohydrate structures present on glycoproteins, proteoglycans, lectin receptors such as the concanavalin A receptor, mucins and enzymes which are involved in the biosynthesis of these molecules such as GalNac transferases and oligosaccharyl-transferases might also serve as normalization markers. The type of marker protein has to be chosen according to the information, which shall be provided by the marker. Principally the markers useful for particular medically relevant conditions may under certain circumstances be useful as normalization markers. A selection of markers useful in performing the methods according to the present invention are given in Table 1.

As well concerning markers for medically relevant conditions as well as concerning normalization markers modified states of molecules (such as polypeptides and nucleic acids) may be used as markers in the method according to the present invention. For example phosphorylated, glycosylated or otherwise modified polypeptides or methylated nucleic acids may be addressed as markers in the method according to the present invention.

Normalization as used according to the present invention shall comprise any method suitable for relating the detected levels of markers to parameters valuable for the assessment of the diagnosis. One aspect of this normalization may be a reconstruction of the relevant cytological and histological information contained within the raw sample by means of suitable molecular markers detectable in the sample solutions. Normalization may comprise for example the detection of the total number of cells present in the sample, of the presence or absence of a particular cell types in a sample, of the presence or absence of an organism or of cells of an organism in a sample, of the number of cells of a particular cell type or organism present in the sample, of the proliferative characteristics of cells present in the sample or of the differentiation pattern of the cells present in the sample.

In certain embodiments normalization may also comprise proving the adequacy of the test, wherein as the case may be inadequate test results may be discarded or classified as invalid. Therefore, normalization as used in the context of the present invention may comprise qualitative or semi-quantitative methods for normalization. In certain embodiments, semi-quantitative normalization may comprise determining a threshold value for a normalization marker. In one embodiment, semi-quantitative normalization may be applied e.g. as follows: the level determined for the relevant marker may be regarded as a valid test result only if the level of the normalization marker exceeds a defined threshold value; in case the threshold value is not reached the test result for the relevant marker is regarded as invalid; diagnosis may not be assessed on the basis of the test. In other embodiments a threshold may be set that may not be exceeded. In certain embodiments, qualitative normalization may be performed with respect to the presence or absence of a normalization marker. In those cases, e.g. the value determined for the relevant marker is compared to the presence or absence of a normalization marker. As predefined, the value is valid only in case the normalization parameter (presence or absence of a detectable level of the normalization marker) is met.

TABLE 1

| marker for | cell type | antigen | Antibody | supplier | Literature |
|---|---|---|---|---|---|
| cell type | epithelial cells | human epithelial cell surface glycoprotein | HEA125 IgG1 (W, IHC, ICC, IF) | Research Diagnostics Inc. | Kommoss et al., Hum Pathol. 2000 Sep;31(9):1055-61 |
| | | Human epithelial proliferation 40 kD protein (from LoVo) | AUA-1 IgG1 (Elisa) | Research Diagnostics Inc. | Gottschalk et al, Pathol Res Pract. 1992 Feb;188(1-2):182-90 |
| | | Human epithelial antigen (34 + 39 kD) | Ber-EP4, IgG1 (IHC, Elisa) | Dako | Latza U et al., J Clin Pathol. 1990 Mar;43(3):213-9 |
| | | Human epithelial proliferating antigen (40 kD) | AUA-1 (Elisa, W, IHC) | Research Diagnostics Inc. | Epenetos, A et al., Lancet. 1982 Nov 6;2(8306):1004-6 |

TABLE 1-continued

| marker for | cell type | antigen | Antibody | supplier | Literature |
|---|---|---|---|---|---|
| | endocervix columnar cells | Cytokeratin 18 (45 kD) | RGE 53, IgG1 (W, IHC, IF) | Research Diagnostics Inc. | Smedts F et al., Am J Pathol. 1990 Mar;136(3):657-68 |
| | | Cytokeratin 18 (45 kD | RCK 106 (W, IHF, IHC) | Research Diagnostics Inc | Smedts F et al., Am J Pathol. 1990 Mar;136(3):657-68 |
| | | Cytokeratin 8 (52.5 kD) | CAM 5.2 (W, IHC) | BD PharMingen | Smedts F et al., Am J Pathol. 1990 Mar;136(3):657-68 |
| | Endocervical columnar cells | Mucin Antigens (Tn, STn, MUC1, MUC2 | DF3 | Centocor | Tashiro et al., Hum Pathol. 1994 Apr;25(4):364-72 |
| | Endocervic Columnar Cells | Concanavalin A receptor | | | Herckenrode et al., Br J Cancer. 1988 Mar;57(3):293-4; Koch et al., Br J Cancer. 1986 Jan;53(1):13-22 |
| | Endocervix | GalNacTransferase Oligosaccharyltransferase | | | Chilton et l., Endocrinology. 1988 Sep;123(3):1237-44 |
| | Endocervic/ Ectocervix | Lectins (ConA, WGA, PNA, UEA I, DBA, SBA, SNA | | | Di Loretto et al., Basic Appl Histochem. 1987;31(2):143-52; Versura et al., Basic Appl Histochem. 1988;32(2):219-27 |
| | ectocervix squamous cells | Plakophilin (80.5 kD | PP1-5C2, IgG1 (W, Elisa, IHC, IF) | Research Diagnostics Inc. | Heid, HW, Differentiation. 1994 Dec;58(2):113-31 |
| | endometrial cells | Vimentin | VIM 3B4, IgG1, (W, ELISA, IF, IHC) | Research Diagnostics Inc. | Smedts F et al., Am J Pathol. 1990 Mar;136(3):657-68 |
| | Erythrocytes | Haemoglobin | RDI-CBL63, IgM (RIA,EIA) | Research Diagnostics Inc. | Smith et al., J. Histochem. Cytochem. 1998 |
| Inflammation | neutrophilic granulocytes NK-cells Macrophages | CD16(NK, Macro, Gran) | DJ130-c, IgG1 (IHC) | DIANOVA | Grundhoever D and Patterson BK, Cytometry 2001;46:340-344 |
| | | CD56(NK) | clone Ki-M6 | | Hermann et al., J. Clin. Immunol. 1990 |
| | | CD68(Macro) | (antiCD68) | | Cavayal et al., Eur. J. Immunol: 1998(6)1991-2002 (CD56) |
| | B-cells | CD19 (CD20) | clone AE 1, FACS | DIANOVA | Harrada et al., Blood 1993;81:2658-63 (CD19) Mason et al., Am J. Pathol1990;136:12 15-22(CD20) |
| | T-cells | CD3 (panTcell) (CD4); (CD8) | clone CRIS-7 (antiCD3); IF, IHC, WB | DIANOVA | Jones et al., J Immunol 1993; 150:5429-35 |
| tumor cells | dysplastic and neoplastic cervical cells | p16$^{INK4a}$ | E6H4, D7D7 | MTM | Klaes R., et. al. Int J Cancer. 2001 Apr 15;92(2):276-84 |
| | different cancer cell types | P53 (mutations) | | | Mendoza-Rodriguez CA, et al., Rev Invest Clin 2001 May-Jun;53(3):266-73 |
| | adeno-carcinoma cells | CEA | | | Mistretta et al., Experientia. 1974 Oct 15;30(10):1209-10; Rogers et al., Eur J Cancer Clin Oncol. 1984 Oct;20(10):1279-86 |

TABLE 1-continued

| marker for | cell type | antigen | Antibody | supplier | Literature |
|---|---|---|---|---|---|
| | bladder cancer cells | NMP22, BTA | | | van der Poel HG et al., Curr Opin Urol,11,503-509, 2001 |
| | lung cancer cells | PreproGRP | | | Hamid et al., Cancer, 63, 266-271, 1989, Pagani et al., Int. J. Cancer 47, 371-375, 1991 |
| Proliferation | all proliferating cells | PCNA Ki67 | Pc10, IgG2a | Zymed | Waseem NH, Lane DP, J Cell Sci 1990:96:121 (PCNA) Cattoretti et al., J Pathol 1992: 168:357-63(Ki67) |
| Infectious agent | HPV 16 | E6 | BF 7, IgG1 (IHC and in diagnostic kit for cervical swabs) | Research Diagnostics Inc. | Iftner et al., J Virol. 1988 Oct;62(10):3655-61 |
| | | L1 | Cam Vir-1, IgG2a (IP, W, IF, IHC) | Research Diagnostics Inc. | Browne L et al., J Gen Virol. 1988 Jun;69 (Pt 6):1263-73 |
| | HPV 18 | L1 | RDI-HPV18-5A3, IgG1 (W, IHC) | Research Diagnostics Inc. | Iftner et al., J Virol. 1988 Oct;62(10):3655-61 |
| | HPV 6,11,18 | | RDI-HPVX-4C4 | Research Diagnostics Inc. | Iftner et al., J Virol. 1988 Oct;62(10):3655-61 Gouillou et al, Am. J. Surg. Pathol., 1991 |

According to the present invention the normalization may comprise the determination of the presence of a number of (human) cells in question in a sample. This is a crucial aspect of the invention. In particular, embodiments false (especially false negative) results of tests can only be avoided, if the testing procedure verifies, that the test sample contains the materials (e.g. cells, tissues organisms etc.), that are necessary for performing the particular test. In various tests this will comprise ensuring, that the sample contains cells. In a wide range of embodiments of the invention the verification of the adequacy of the sample will not just comprise ensuring of the presence of cells, but will include the detection of the presence of cells of a distinct origin or of a special cell type.

Thus normalization may also comprise the determination of cells of particular origin such as e.g. cells from a particular organ or of a particular histological localization such as for example the detection of cells of distinct regions of epithelia, or of cells of connective tissue, cells originating from the basal lamina of a tissue or of cells of a heterologous origin, such as metastatic cells. This may be necessary in particular cases, because there might be cells, that under certain circumstances do express a marker, which might be used for the detection of a medically relevant condition, such as e.g. neoplasia or dysplasia, under certain normal conditions. Normalization as used according to the present invention may comprise the detection of the presence or absence and/or the level of any cell-types, that may possibly contribute to the total level of a particular marker selected to diagnose a medically relevant condition.

In one embodiment, the method may be applied for the detection of cervical lesions. Cervical lesion may comprise any kind of cervical dyplasia such as cervical cancers as defined above and its precursory stages. Markers and combinations thereof useful for this detection purpose are for example disclosed in WO0208764 and EP1217377, which documents shall be incorporated herein by reference. In this embodiment the test may be performed using any suitable sample of cervical origin. The sample may for example comprise biopsies or microbiopsies of the cervix or swabs taken from the cervical region. Cervical swabs as used herein are samples that may for example be obtained using a suitable device such as a brush, a tampon, a spatula or the like, which is contacted with the uterine cervix during the sampling procedure. The sampling device may be any suitable device, which may be used in conventional testing performed by a physician or a self sampling device.

Promising molecular markers for enhancing the evaluation of cervical swabs are e.g. $p16^{INK4a}$, p14ARF, cyclin E, cyclin A, cyclin B, MN, her2/neu, mdm-2, bcl-2, EGF-Receptor, mcm-2, mcm-5, claudin-1, Markers indicative for Human papilloma virus infection, pRb, p53 etc. which might be used to detect dysplastic and neoplastic cells. Normalization according to the present invention for the purpose of analysis of cervical swabs may comprise the detection of the presence of human cells at all, the detection of cells of the cervical epithelium, the detection of the presence of endocervical as well as ectocervical cells and the detection of cells of endometrial origin. The endocervical epithelium is a glandular columnar epithelium. Cells originating from the endocervix may thus be identified by markers that are selectively expressed by columnar epithelial cells or by cells in glandular epithelia. The ectocervical epithelium is a squamous epithelium. Identification of ectocervical cells thus may be achieved by detection of markers characteristic for squamous epithelial cells. In certain embodiments, the detection of epithelial cells (comprising squamous as well as columnar epithelia) may be sufficient. In other embodiments, the differentiation of especially endocervical cells may be crucial. It is a crucial step to ensure the presence of ecto- and endocervical cells within the sample to ensure, that the specimen was taken at the cervical transformation zone, where most dysplasias and neoplasias arise. If there are no such cells, the sample is not adequate for the testing procedure, for it is prone to give false negative results. As $p16^{INK4a}$ may be expressed in normal endometrial cells normalization of the $p16^{INK4a}$ expression level in regard to the number of endometrial cells might be necessary.

To enable for reliable diagnosis the normalization furthermore may comprise the detection of the presence or absence of the named cellular components within the sample, and additionally the detection of the total level of a particular cell type or of the fraction, that a particular cell type contributes to the total number of cells within the sample.

Thus, in one embodiment the detected level of the $p16^{INK4a}$ protein may be normalized to the cytological conditions represented by the particular sample, so that one may state, if the detected level of the $p16^{INK4a}$ protein is indicative for cervical cells overexpressing $p16^{INK4a}$, or if there is an abundant number of endometrial cells present in the sample, thus mimicking the overexpression of $p16^{INK4a}$. In this respect normalization may comprise the determination of the quantity of endometrial cells within a cervical sample on the basis of a molecular marker. Comparing the level of e.g. $p16^{INK4a}$ as a marker for a medically relevant condition determined in a cervical sample to the quantity of endometrial cells assessed by means of molecular markers, one may state, whether the total amount of p16 may arise only from the endometrial cells present within the sample solution. Thus, false positive results in diagnosing cervical dysplasias overexpressing $p16^{INK4a}$ attributable to the presence of high levels of endometrial cells may be excluded. A quantity as used in the context of the present invention may refer to a quantitative or semi-quantitative assessment. This may e.g. comprise the assessment of a total number of cells or the assessment of a fraction with respect to the total number of cells. In certain embodiments of the invention the determination of a quantity may refer to the assessment of the fraction of an overall marker level that is contributed by a particular type of cells.

For the purpose of providing a normalization marker for the evaluation of cervical specimens, several normalization markers appear to be useful and may e.g. be selected from the following: Cytokeratins, E-Cadherins, Involucrin, Urokinase-like Plasminogen-activator, SCCA (Squamous cell carcinoma antigen), Catenins, (e.g. alpha-catenin, beta-Catenin, gamma-Catenin (Plakoglobin)), Ep-Cam.

Several candidates for normalization markers have been examined for their properties in characterization of cervical specimens. The results are given in Table 2 and Table 3.

TABLE 2

| Name | Histology/Cytology | Clinical/Biochemical Data | Literature |
| --- | --- | --- | --- |
| UPA-1 (Urokinase-type Plasminogen-Activator; Swissprot Accession P00749; also known as EC 3.4.21.73, U-plasminogen activator uPA) | Cervical tissue Normal epithelium showed presence of both t-PA and u-PA immunoreactivity only in the superficial cellular layer, whereas in preinvasive lesions they were present in all layers. | ↑ In cervix CA | Horn LC Aust N Z J Obstet Gynaecol, 2002 Lesson G Throb. Haemost. 1987 |
| PAI-1 (Plasminogen-Activator Inhibitor 1; Swissprot Accession P05121; also known as PAI-1 Endothelial plasminogen activator inhibitor PAI; Isoforms: PAI-2 P05120 and PAI-3 P05154) | Cervical tissue Normal epithelium showed presence of both t-PA and u-PA immunoreactivity only in the superficial cellular layer, whereas in preinvasive lesions they were present in all layers. | ↑ In cervix CA positive prognostic marker | Horn LC Aust N Z J Obstet Gynaecol, 2002 Larsson G Thromb. Haemost. 1987 |
| Involucrin (Swissprot Accession P07476) | Only squamous epithelia, no columnar cells; immature and mature squamous metaplastic cells. In normal epidermis, it is first expressed in the upper spinous layers, and in keratinocyte cultures it is expressed by all cells that have left the basal layer. | Involucrin expression is abnormal in squamous cell carcinomas and premalignant lesions, and is reduced in severe dysplasias of the larynx and cervix. Marker for terminal differentiation. | Shirley A, Human Pathology, 2001 de Boer et al., 1999, Am J of Pathol, 155:505-515 Nair SA, Pathobiology, 1996 |
| gamma-Catenin (Swissprot Accession Q86W21; also known as Plakoglobin; e.g. Epitope: C-Terminus; AA553-738) | Squamous epithelia | High in normal cervical epithelium at cell-cell-boundaries. Moderate reduction in high grade SILS | de Boer et al., 1999, Am J of Pathol, 155:505-515 |

TABLE 2-continued

| Name | Histology/Cytology | Clinical/Biochemical Data | Literature |
|---|---|---|---|
| Alpha-1 Catenin (Swissprot Accession P35221; also known as Cadherin-associated protein Alpha E-Catenin) SEQ ID NO: 4 | Squamous epithelia | High in normal cervical epithelium at cell-cell-boundaries Strong reduction in high grade SILS | de Boer et al., 1999, Am J of Pathol, 155:505-515 |
| Alpha-2 Catenin (Swissprot Accession P26232; also known as Alpha-Catenin related protein Alpha N-Catenin) SEQ ID NO: 5 | | | |
| beta-Catenin (Swissprot Accession P35222 also known as PRO2286) SEQ ID NO: 6 | Squamous epithelia | High in normal cervical epithelium at cell-cell-boundaries Strong reduction in high grade SILS | de Boer et al., 1999, Am J of Pathol, 155:505-515 |
| Desmoplakin (Swissprot Accession P15924; also known as DP 250/210 kDa paraneoplastic pemphigus antigen) | stratified epithelia, simple epithelia, including glands, urothelium, thymic reticular epithelium, hepatocytes, intercalated disks of myocardium and arachnoid cells of meninges suprabasal layers of cervix (Superficial cells largely negative) | ↓ in HSIL area | de Boer et al., 1999, Am J of Pathol, 155:505-515 |

↓: down regulated; ↑: up regulated;

TABLE 3

| Marker | Histological testing | Cytological testing | Western Blot Analysis (clinical samples were freshly lysed with MTM buffer) |
|---|---|---|---|
| E-Cadherin (Swissprot Accession P12830; also known as Uvomorulin, Cadherin-1, CAM 120/80; e.g.epitope: C-Terminus; AA735-883) SEQ ID NO: 3 | Squamous epithelia, (Parabasal, intermediate cells) no columnar epithelia | Parabasal, intermediate cells, no columnar cells | Only weak signal for HT-29. All clinical samples are negative |
| p120 Swissprot Accession O60716; p120 catenin, p120(ctn), Cadherin-associated Src substrate, CAS, p120(cas); e.g.epitope: C-Terminus; AA790-911) SEQ ID NO: 8 | Squamous epithelia, (Parabasal, intermediate cells) also very strong in columnar epithelia | Very strong staining of parabasal, intermediate cells strong columnar cells | Only negative control (lymphocytes) and positive control (C4.1) positive |
| gamma-Catenin Swissprot Accession Q86W21; also known as Plakoglobin; e.g. epitope: C-Terminus; AA553-738) SEQ ID NO: 1 | Squamous epithelia, (Parabasal, intermediate cells) no columnar epithelia, total epithelium is stained indysplasia | Very strong staining of parabasal, intermediate cells no columnar cells | Double bands (82/95 kD) in 60% of samples (9/15); after acetone precipitation of 150 μl of samples: 87% (13/15) positive |
| Ep-Cam (Tumor-associated calcium signal transducer 1, Swissprot Accession P16422; also known as Major gastrointestinal | strong columnar epithelia, at very high concentrations rather unspecific (cytoplasmic) staining of squamous epithelia, | strong columnar cells, at very high concentrations rather unspecific (cytoplasmic) staining of squamous epithelia, (Parabasal, | |

TABLE 3-continued

| Marker | Histological testing | Cytological testing | Western Blot Analysis (clinical samples were freshly lysed with MTM buffer) |
|---|---|---|---|
| tumor-associated protein, GA733-2, Epithelial cell surface antigen, Epithelial glycoproteins, EGP, Adenocarcinoma-associated antigen KSA KS 1/4 antigen Cell surface glycoproteinTrop-1) SEQ ID NO: 2 | (Parabasal, Intermediate Cells) | Intermediate Cells | |
| Involucrin (Swissprot Accession P07476) SEQ ID ON: 7 | Strong staining of squamous epithelia, (Parabasal, Intermediate Cells) and columnar epithelia; unspecific staining of stromal cells; | All cells and structures positive | |

The markers for normalization may for example be applied as markers indicative of the presence of specific cell differentiation patterns such as e.g. terminal differentiation or differentiation as specific epithelial cells. In certain embodiments, normalization markers may be marker molecules characteristic for squamous epithelial cells e.g. indicative for the presence of ectocervical cells in a cervical sample. Suitable markers may comprise e.g. CK13, E-Cadherin, gamma-Catenin, or Involucrin. In another embodiment the markers may be characteristic for the presence of columnar epithelial cells indicating the presence of endocervical cells in the specimen. Suitable markers comprise: Ep-Cam, CK18, CK8.

In certain embodiments, normalization may comprise the detection of epithelial cells generally; in these cases any marker suitable for the detection of epithelial cells may be employed. Markers may be for example those given in Tables 2 and 3.

In yet another embodiment of the invention, the method disclosed herein may be used for the detection of disorders of the respiratory tract. In the diagnosis of small cell lung cancer detection of neuron specific enolase (NSE) is one of the employed markers. Samples of tumor specimens are yielded by bronchoscopy with collection of cells by means of brushes or bronchoalveolar ravages. Since NSE is also expressed in few normal cells within the lung, the level of NSE expression detected in the dissolved sample has to be set in relation to the normalisation maker (for example actin) for detection of the amount of cells present within the sample.

A third embodiment of the present invention is the detection of lesions of the gastrointestinal tract, e.g. colorectal lesions from stool samples. In this case the origin of indicative nucleic acids and/or polypeptides detectable in stool samples may be crucial for the assessment of diagnosis. According to the present invention, it is possible to determine the origin (cell types/organism) of the employed marker molecules. Thus false results based e.g. on the detection of marker molecules originating from foodstuff ingested by individuals rather than from lesion of the mucosa of the gastrointestinal tract may be eliminated. Furthermore artefacts produced by the presence of traces of markers from the blood circulation, or originating from swallowed sputum etc. may be eliminated using the methods disclosed herein.

Another aspect of the present invention is a testing kit for performing the method according to the present invention. The kit may be for example a diagnostic kit, an analytical kit or a research kit.

The term kit as used according to the present invention may comprise kits as well as diagnostic devices. The kits or devices may e.g. be designed for ELISA (e.g. sandwich, competitive, non-competitive, etc.), EIA (competitive, non-competitive, etc.) RIA tests, bead based test systems, lateral flow assays, flow through assays, strip test assays, dip stick assays, or any other known laboratory-, bench top- or point of care-testing format. A kit according to the present invention may in certain embodiments comprise in-vitro diagnostic devices for performing diagnostic tests. In vitro-diagnostic devices may e.g. be ELISA devices of any kind known to those of skill in the art. These devices comprise devices for sandwich ELISA formats, for competitive ELISA formats and any other ELISA formats. In another embodiment the in-vitro diagnostic device may be a lateral flow assay device, or a flow through assay device e.g. employing at least one reagent binding to a marker characteristic for a medically relevant condition and one reagent binding to a normalization marker, both fixed to a solid phase. Such devices may employ various mechanisms for visualization of the test result. In certain embodiments the tests may employ secondary detection reagents directed against the marker molecules coupled to detectable moieties. The detectable moieties may comprise colloidal gold, (coloured) latex particles and others.

In yet another embodiment the in-vitro diagnostic test device may be a flow through assay device based on capillaries or on porous members (such as membranes, beads or other three dimensional arrangements of porous substances). Depending on the embodiment the size of pores or capillaries need to be adjusted to ensure optimal flow conditions.

A kit according to present invention may comprise a) reagents for the detection of the marker molecules, b) the reagents and buffers commonly used for carrying out the detection reaction, such as buffers, detection-markers, carrier substances and others, c) one or more markers and/or samples representative for medically relevant conditions to be diagnosed for carrying out positive and/or control reactions, and d) one or more normalization marker samples for carrying out a positive and/or control reaction.

The test kit may optionally include a lysis buffer for solublization of the raw sample. Generally the lysis buffer may be any suitable solvent known to those of skill in the art. The lysis buffer for use in the kit may for example be aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), non-ionic detergents (e.g. TWEEN®-20, nonidet P-40, TRITON® X-100, NP-40, IGEPAL® CA 630, N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH.

raw samples. Such components may for example comprise enzyme inhibitors such as proteinase inhibitors, RNAse inhibitors, DNAse inhibitors etc. The inhibitors may e.g. comprise proteinase inhibitors selected from the compositions given in Table 5. In certain embodiments the lysis buffer by the way of providing an inhibitor of degradation enables for detection of p16 in the sample. In certain embodiments the cyclin dependent kinase inhibitor p16 is degraded in the solubilized samples and may thus not be detected. This is espe-

TABLE 4

| Lysis buffer | Solubilization of p16INK4a in Western blot | compatibility with Elisa |
|---|---|---|
| Detergents: | | |
| 0.1-1% SDS | + | +/− |
| 0.2-3% SDS | + | <0.5% |
| 0.2-3% DOC | ++ | +/− |
| 0.1-1% n-Octylglycoside | + | yes |
| 0.1-3% TRITON ® X-100% | + | yes |
| 0.1-1% Chaps | + | nd |
| Detergent-Mix: | | |
| RIPA (1%NP40, 0.5%DOC, 0.1%SDS, PBS) 40-100% | ++ | yes |
| SOX (0.5% DOC, 0.5% n-Octylglycoside) 40-100% | + | yes |
| mtm lysis buffer (3% TRITON ® X-100, 0.4% SDS, PBS) | ++ | yes |
| Commerical lysis buffers: | | |
| Dynal (Dynal, Oslo, Norway) | ++ | yes |
| M-PER/B-PER (Pierce, Rockford, IL) | ++ | yes |
| Miscellaneous: | | |
| 0.5-8 M urea in PBS | +++ | Compatible <2 M |
| Lämmli sample buffer | +++ | no |
| 10-80% DMSO | +++ | no |
| 10-80% Formamide | nd | no |
| 50-70% formic acid | ++ | no |
| PBS | +/− | yes |
| Citrate buffer pH 6.0 | +/− | yes |
| 500 mM NaCl in Phosphate buffer | +/− | yes | nd: not determined; +/−: poor; +: good; ++: very good; +++: excellent;

The lysis buffer may furthermore comprise one or more agents that prevent the degradation of components within the cially true, if the samples are directly transferred to a lysing medium and stored therein for a certain period of time.

TABLE 5

| Inhibitor | Class of inhibited proteinase | concentration | Solubility in water | stability in water |
|---|---|---|---|---|
| Aprotinin | Serine | 0.6-2 µg/ml | Very good | good |
| Benzamidine | Serine | 0.5-4 mM | good | good |
| Bestatin | Aminopeptidases | 1-10 µM | good | good |
| Calpeptin | Cysteine | 0.3-1 µM | good | good |
| Cystatin | Cysteine | 1 µM | good | good |
| E-64 | Cysteine | 1-10 µM | good | good |
| EDTA | Metallo | 0.5-5 mM | good | good |
| Elastatinal | Serine | 0.5-2 µg/ml | poor | good |
| EST | Cysteine | 20-50 µg/ml | bad | poor |
| Fetal calf serum | all classes | 10% | good | good |
| Leupeptin | Serine/Cysteine | 10-100 µM | good | good |
| a2-Macroglobulin | all classes | 1 µM | good | good |
| NCO-700 | Cysteine | 0.5-100 mM | poor | poor |

TABLE 5-continued

| Inhibitor | Class of inhibited proteinase | concentration | Solubility in water | stability in water |
|---|---|---|---|---|
| Pefabloc = AEBSF | Serine | 0.2-10 µM | good | very poor |
| Pepstatin A | Aspartic | 1 µM | bad | poor |
| PMSF | Serine | 0.2-10 µM | bad | very poor |
| o-Phenanthroline | Metallo | 1-10 mM | bad | poor |

For stabilization purpose the lysis buffer may also comprise bulk protein (e.g. albumin such as bovine serum albumin or calf serum albumin or other bulk proteins) to compete in degradation with the sample proteins. The bulk proteins may e.g. be present in combination with proteinase inhibitors or may be added instead of proteinase inhibitors. In one embodiment the solvent may be selected to be compatible with the performance of the test (EIA, ELISA or strip test performance), so that solubilized samples may directly be applied to the test. Test as used in the context may comprise any procedure for detecting the presence or absence and/or the level of marker molecules.

The reagent for the detection of the marker molecules may include any agent capable of binding to the marker molecule. Such reagents may include proteins, (poly)peptides, nucleic acids, peptide nucleic acids (PNAs), glycoproteins, proteoglycans, polysaccharids or lipids.

The markers characteristic for medically relevant conditions and/or normalization marker samples for carrying out positive and/or negative controls may comprise for example nucleic acids in applicable form such as solution or salt, peptides in applicable form, tissue section samples, microorganisms or positive or negative cell-lines.

In one embodiment of the invention, the detection of the marker molecules is carried out on the level of polypeptides. In this embodiment the binding agent may be for example an antibody specific for the marker molecules or a fragments thereof. Furthermore binding agents may comprise antigen-binding fragments such as Fab fragments, single chain antibodies, bifunctional hybrid antibodies, peptidomimetics containing minimal antigen-binding epitopes etc. Moreover the binding agent might be a lectin binding to a specific carbohydrate structure on the marker molecule.

In another embodiment of the test kit the detection of the marker molecules is carried out on the nucleic acid level. In this embodiment of the invention the reagent for the detection may be for example a nucleic acid probe or a primer reverse-complementary to said marker nucleic acid.

The following examples are given for the purpose of illustration only and are not intended to limit the scope of the invention disclosed herein.

EXAMPLES

Example 1

Specific Immunohistochemical Detection of Endocervical and Ectocervical Epithelial Cells in Cervical Sections In order to evaluate markers indicating the adequacy of cervical swabs, cervical sections (fixed in 4% formaldehyde solution and paraffin-embedded) were stained with antibodies directed against Cytokeratin 18 (marker for endocervical columnar epithelia) and Cytokeratin 10/13 (marker for ectocervical squamous epithelia). FIG. 1 shows specific staining of endocervical epithelia with anti-Cytokeratin 18 antibody and specific staining of ectocervical epithelia with anti-Cytokeratin 10/13 antibody. The experiment was performed as follows:

Formalin-fixed, paraffin-embedded sections were deparaffinized in xylene bath for 5 min (step was repeated once), excess liquid was tapped off and slides were placed in 95-96% ethanol for 3 (±1) min, in 70% ethanol for 3 (±1) min (step was repeated once) and finally in distilled water for a minimum of 30 sec. For epitope retrieval, slides were placed in a Coplin jar and boiled for 40 min at 95-99° C. in 10 mM Citrate buffer pH 6.0. Slides were allowed to cool down for 20 min (±1 min) at RT in this buffer. Slides were covered with Peroxidase-Blocking Reagent (3% $H_2O_2$; $NaN_3$ 15 mM) and incubated for 5 (±1) min at RT. After 5 min washing in washing buffer, slides were incubated with primary antibodies (CK 10/13: DE-K13, 1:50, DAKO; CK 18: K18.7, 1 µg/ml, dianova) for 30 min. Thereafter, slides were rinsed with wash buffer and washed in wash buffer for 5 min at RT. Following 30 min incubation with EnVision (ready to use anti-mouse horseradish peroxidase-complex; DAKO), slides were washed 3×5 min and incubated in DAB substrate for 10 min, counterstained with hematoxylin and mounted with Faramount mounting medium.

Using an antibody directed against cytokeratin 18 (CK18) in an immunohistochemical staining procedure, a positive reaction was detected in columnar epithelium of the endocervix (FIG. 1A), whereas the squamous epithelium of the ectocervix showed no specific staining (FIG. 1B). Immunohistochemical staining with an antibody directed against cytokeratin 10/13 (CK 10/13) showed no staining in the columnar epithelium of the endocervix (FIG. 1C), whereas there is a strong staining of the squamous epithelium of the ectocervix (FIG. 1D). So CK18 might be used as a specific marker for the detection of columnar epithelial cells of the endocervix and CK10/13 as a specific marker for squamous epithelial cells of the ectocervix.

Example 2

Western Blot Analysis of Solubilized Samples from Cervical Swabs

In order to evaluate, whether western blot analysis of solubilized samples allows assessing diagnosis of cervical lesions, clinical samples with known diagnosis were subjected to an immuno-chemical analysis on the basis of marker molecules after lysis of the sample material.

The clinical material (cervical swabs) samples were analyzed by Standard Western Analysis as follows.

In brief, the clinical material was in a first step solubilzed by boiling (5 min, 95° C.) in Larmli Protein Sample buffer (100 mM Tris pH.6.8, 2% SDS, 200 mM DTT, 0.05% BpB) prior to sonification. In a second step, protein samples were resolved on a SDS-PAGE (12% Acrylamide) and subsequently transferred on a nitrocellulose membrane by tank blotting (Towbin et al., 1979, Proc Natl Acad Sci: 76:4350-4354). In a further step, the membranes were: blocked to prevent unspecific antibody binding (10% non fat dry milk in PBS) and subsequently incubated with the specific monoclonal mouse antibody (CK 8: 35βH11, 1:100, DAKO; p16$^{INK4a}$: D7D7, 1:140, MTM Laboratories). The binding of the specific antibody was visualized by Horseradish Peroxidase conjugated secondary reagents (binding to the marker specific antibody) catalyzing photon emitting substrates.

Cytokeratin 8 (CK 8) was used as an endocervical cell specific marker, indicating the adequacy of the sample collection in the present experiments. The cyclin dependent kinase inhibitor p16$^{INK4a}$ was used as specific disease related marker.

Figure 2:
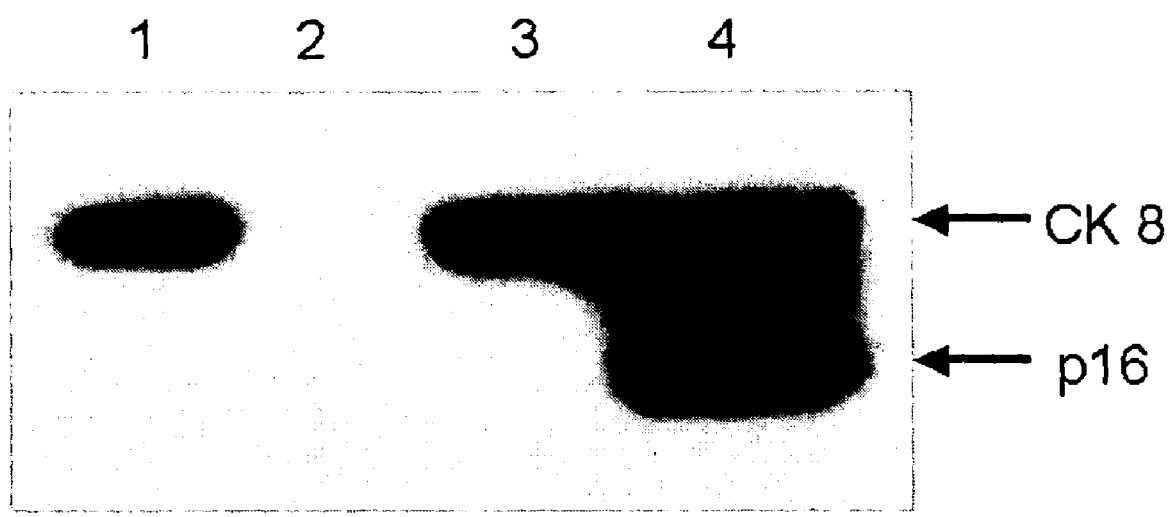
FIG. 2 shows the Western Blot analysis of solubilized samples from cervical swabs. The numbers 1 to 4 refer to samples (cervical swabs) obtained from individual patients

The results of the present experiment are given in FIG. 2. The numbers 1 to 4 refer to samples (cervical swabs) obtained from individual patients. Immunoblot detection was performed using specific antibodies directed against cytokeratin 8 (CK8) and specific antibodies directed against p16$^{INK4a}$ (p16). The samples of patient 1, 2, and 3 show no signal for p16$^{INK4a}$. This indicates that no dysplastic cervical cells were present in these samples. The sample of patient 4 shows a strong signal for p16$^{INK4a}$. This indicates that dysplastic cervical cells were present in the sample. The upper bands show the specific signals for cytokeratin 8. In sample 1, 3, and 4 cytokeratin 8 can be detected, whereas in for sample 2 no signal can be seen. This indicates that endocervical columnar cells were present in samples 1, 3, and 4, and absent in sample 2. As the presence of endocervical columnar epithelial cells is one of the parameters for the adequacy of cervical swabs, sample 2 is considered inadaequat and no diagnostic conclusions can be drawn from the negative result of the p16$^{INK4a}$ detection. Samples 1, 3, 4 are considered adequate. So based on the negative signal of sample 1 and 3 for p16$^{INK4a}$ it could be concluded, that these patients had no cervical dysplasia. Sample 4 showed a positive signal for p16$^{INK4a}$, indicating the presence of a dysplastic cervical lesion in this patient.

The parallel cytological analysis of the swabs indicated a normal cellular composition for woman 1 and 3. In women 2, no diagnosis due to sparse cellular material could be obtained. In woman 4, a high-grade dysplasia was diagnosed. Note that the upper band (CK 8) refers to the endocervical cell specific normalization marker Cytokeratin 8, indicating the adequacy of the sample collection. The lower band indicates the specific disease related marker p16$^{INK4a}$ The blot shows for patient 4 a positive signal for p16$^{INK4a}$ consistent with a high-grade cervical dysplasia. Samples of patient 1 and 3 show only the CK 8 specific band, indicating proper sample collection, but no disease related marker (p16$^{INK4a}$) consistent with a normal, healthy cervical epithelium. The sample of patient 2 shows no CK 8 signal, consistent with the low cell number in this sample, so no diagnostic conclusion can be drawn from the negative signal for p16$^{INK4a}$.

Example 3

Western Blot and ELISA Analysis to Demonstrate Sample Adequacy

To evaluate, whether results of solution based analysis differing from diagnosis of samples may be due to inadequacy of sample, Western blot analysis of cervical swabs of four different patients with ascertained diagnosis (high-grade cervical intraepithelial neoplasia according to the cytological diagnosis of Pap IVa and Pap IVb) was performed. Antibody against p16$^{INK4a}$ was used to indicate presence of dysplastic cells, whereas antibodies against CK18 and CK10/13 were used to demonstrate adequacy of the sample.

Western blot analysis was performed as follows: Patient samples were collected with a cervical brush and directly lysed in Laemmli Sample Buffer (2% SDS, 60mM Tris pH.6.8, 0.01%, 100 mM DTT) for 5 mm at 95° C. (1×10$^7$ cells/ml) with subsequent sonification (5×5 sec pulses, maximum intensity). Lysates were centrifuged for 12 min at 16,600×g) in a microcentrifuge and supernatant was transferred into a new tube. Precast 4-20% linear gradient acrylamide gels (Criterion System, Bio-Rad) were loaded with 10 µl (10$^5$ cells) of whole cell extracts and proteins were separated at 25 mA constant current for 45 mm. Proteins were transferred from the gel to HYBOND® (Hydrophobic polyvinylidene difluoride membrane) ECL Nitrocellulose membrane (Amersham) by standard tank blotting using the Bio Rad Criterion Blotter (15 min at constant 100 Volt and subsequently 45 min at constant 50 Volt). Nitrocellulose-membrane was stained for 5 min in Ponceau S solution to assure protein transfer. Ponceau S solution was removed by 2×10 min washes in PBS. For immunodetection, blots were blocked over night in blocking buffer (10% milk powder in PBS with 0.1% TWEEN®-20). Primary antibodies were incubated at dilutions according to the manufacturer in blocking buffer for 1 h at RT with agitation (CK18: MAB 3236), 1:1000, CHEMICON; CK 10/13: DE-K13, 1:500, DAKO, p16$^{INK4a}$: D7D7, 1:140, MTM Laboratories). After 6 washes for 10 min with PBS/0.1% TWEEN®-20), blots were incubated with rabbit anti mouse-HRP, (DAKO, diluted 1:5,000 in blocking buffer) for 1 h at RT. After 6 washes for 10 min with PBS/0.1% TWEEN®-20), membranes were incubated for 5 min in substrate solution (Super Signal West Femto Maximum Substrate, Pierce), wrapped in a plastic envelope and exposed to an x-ray film for 1-5 min. Finally, x-ray films were developed, fixed, dried and documented with an imaging system (Bio-Rad). The same samples were used to perform ELISA analysis for p16$^{INK4a}$, CK 10/13, CK18. The detected signals and results were the similar to the Western blot analysis and the same conclusions were drawn.

The ELISA analysis was performed as follows: Flat bottom 96 well plates (MAXISORB®, chemical product; Nunc) were coated with capture antibody (p16$^{INK4a}$: MTM-E6H4, 2 µg/ml in PBS, MTM Laboratories; CK10: MS481P1ABX, 2 µg/ml, dianova; CK18: K18.7, 2 µg/ml, dianova; 50 µl/well) over night at 4° C. Plates were washed 6× with PBS/0.1% TWEEN®-20 and blocked with SUPERBLOCK® buffer (chemical reagent, Pierce). Solubilized protein extract from cervical swabs were dissolved in incubation buffer (PBS, 3% SUPERBLOCK® (Chemical reagent), 0.1% TWEEN®-20), and added in triplicates to each well. After 1 h incubation at RT, plates were washed 6× with PBS/0.1% TWEEN®-20 and incubated with biotinylated detection antibody (p16$^{INK4a}$: MTM-D7D7 (0.2 µg/ml, MTM Laboratories, CK10: MS481-BO, 200 µg/ml, dianova; CK18: MS142-BO, 200 µg/ml, dianova; in incubation buffer) for 1 h at RT. Following 6× washes with PBS/0.1% TWEEN®-20 TMB, 50 µl of Streptavidin-coated Alkaline Phosphatase (1:1000 dilution; Dianova) was added for 30 min. Thereafter, plates were washed 6× with PBS/0.1% TWEEN®-20 and 100 µl of p-nitrophenyl phosphate substrate (PnPP; dissolved in diethanol amine buffer) were added to each well. OD 405 nm (620 nm reference wavelength) was measured with an ELISA reader (TECAN®) after 30 min, 1 h and 2 hrs. The present example shows, that the sandwich ELISA format exhibits sensitivity, which is suitable for the use in the methods according to the present invention. For use in the method disclosed herein the sandwich ELISA format as described in this example may be applied to multiple marker molecules, such as markers for normalization/adequacy and markers characteristic for medically relevant conditions.

Samples of four patients with high-grade cervical dysplasias (see Diagnosis) were analysed using western blot analysis (upper panel of figure). For the left blot immunoblot detection was performed using antibodies specific for β-actin and p16$^{INK4a}$, for the middle blot antibodies specific for cytokeratin 10/13 and for the right blot antibodies specific for cytokeratin 18 were used. β-actin, CK18, and CK10/13 were used as markers demonstrating the adequacy of the sample. β-actin indicates the presence of any cells, CK10/13 the presence of ectocervical squamous cells, CK 18 the presence of endocervical columnar cells.

Figure 3:
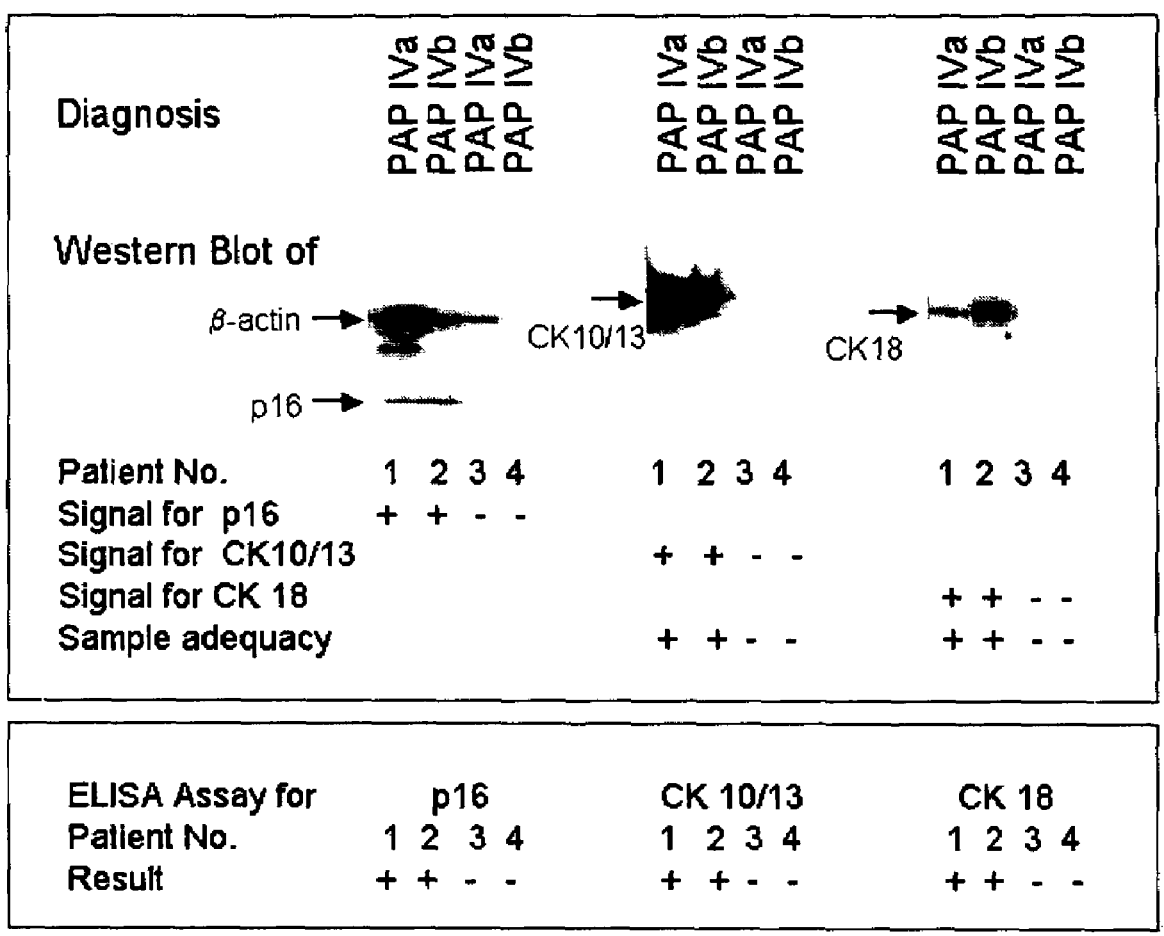
FIG. 3 shows the Western blot and ELISA analysis to demonstrate sample adequacy. Samples of four patients with high-grade cervical dysplasias (see Diagnosis) were analysed using western blot analysis (upper panel of figure). The lower panel of this figure shows the results of ELISA analysis.

As shown in FIG. 3, for the samples of patient 1 and 2, the immunoblot detections show positive signals for all the applied adequacy markers (CK10/13, CK 18, β-actin) and for the marker (p16$^{INK4a}$) indicative of dysplastic cells. Samples 3 and 4 were negative for p16$^{INK4a}$ bands in Western blot. However, in these cases the β-actin and the two cytokeratin markers showed an extremely weak (patient 3, β-actin) or negative (patient 4, all markers; patient 3, CK markers) signal in the Western blot analysis. So no diagnostic conclusion can be drawn from the negative signal for p16$^{INK4a}$.

The lower panel of this figure shows the results of ELISA analysis. Positive signals for the adequacy markers (CK10/13, CK 18) were detected for the sample of patient 1 and 2, whereas for the samples of patients 3 and 4 no signals for CK10/13 and CK 18 was seen. So the ELISA analysis results resemble the Western blot analysis results and the same conclusions can be drawn.

Example 4

Western Blot Analysis of Different Samples of Pulmonary Origin

In order to evaluate, whether Western blot analysis of solubilized samples allows to assess diagnosis of pulmonary lesions, clinical samples with known diagnosis were solubilized and subjected to an immuno-chemical analysis on the basis of marker and normalization molecules.

The clinical samples (cells collected by brushing or bronchoalveolar lavage) were analyzed by Standard Western Analysis as follows. Cells from bronchoalveolar lavage were pelleted by centrifugation (5 min, 1000 rpm) and the pellet was dissolved in Lämmli Protein Sample buffer (100 mM Tris pH.6.8, 2% SDS, 200 mM DTT, 0.05% BpB). Cells obtained by brushing were dissolved directly in Lammli Protein Sample buffer (100 mM Tris pH.6.8, 2% SDS, 200 mM DTT, 0.05% BpB). The material was boiled (5 min, 95° C.) prior to sonification. In a second step aliquots of the protein samples were resolved in duplicates on a SDS-PAGE (12% Acrylamide) and subsequently transferred on a nitrocellulose membrane by tank blotting (Towbin et al., 1979, Proc Natl Acad Sci; 76:4350-4354). In a further step the membranes were blocked to prevent unspecific antibody binding (10% non fat dry milk in PBS) and subsequently one membrane was incubated with specific monoclonal mouse antibodies against NSE (DAKO Germany, clone BSS/NC/VI-H14, mouse monoclonal, dilution 1:1000;) and one membrane was incubated with the normalization marker actin (ICN, USA, clone C4, mouse monoclonal, dilution 1:400). The binding of the specific antibody was visualized by Horseradish Peroxidase conjugated secondary reagents (binding to the marker specific antibody) catalyzing photon emitting substrates.

In the bronchoalveolar lavages of patients with known small cell lung cancers high levels of NSE in comparison with the expression levels of actin was detected, whereas in patients without tumor hardly any NSE could be detected, the actin level however was comparable to the level of the cancer patients. (Data not shown)

The results indicate, that a normalization of the solution based testing procedure according to the method presented herein enables for assessing diagnosis of diseases without relying on morphological information Example 5

Detection of Cervical Intraepithelial Neoplasia in an ELISA Test Format 34 cervical swabs provided in lysis buffer have been subjected to ELISA based detection of overexpression of cyclin dependent kinase inhibitor p16$^{INK4a}$ in solutions prepared from the cells contained in the swabs. The ELISA testing was performed as follows:

(A) Cell Lysis

Cervical swab brushes are given into 15 ml vessels, containing 2 ml of mtm lysis buffer. Cervical cells present in the brush are lysed for at least 20 h. The lysates of the cervical swab samples are then transferred in 2 ml tubes and are centrifuged at 4° C. (15 min at 28.000×g (16.600 rpm High-speed Centrifuge JEC Multi RF)); Supernatant is transferred to a fresh tube. As the case may be the supernatant may be stored at −20 ° C.

(B) Performing the ELISA

Coating of ELISA-plates

Stock-solutions of p16$^{INK4a}$-specific antibody clone mtm E6H4, Ep-Cam specific antibody Ber-Ep4 and gamma-Catenin specific antibody clone 15 are diluted in PBS to give ready-to-use coating solution.

50 µl of each ready-to-use capture antibody coating solution is added to ELISA plates.

For coating, the plates are incubated overnight at 4° C.

Coating solutions are removed from the ELISA plates and the plates are rinsed using an automated ELISA washer as follows:

7×250 µl washing buffer (0.1% TWEEN®-20 (v/v) in PBS)

after removing remnants of the washing buffer, 300 µl blocking buffer (2% BSA in PBS) is added to each well. Plates are incubated for 1 h on a rocking device at ambient temperature.

Incubation with Samples

After removing the blocking buffer 100 µl of the lysed cell sample is added to each well. Lysates of HeLa-cells are used as positive control for antibodies specifically detecting p16$^{INK4a}$ and gamma-Catenin; Lysates of HT29-cells are used as positive control for antibodies specifically detecting Ep-Cam;

For purpose of calibration of the test, different concentrations of recombinant p16 protein, recombinant gamma-Catenin and Ep-Cam (0 pg/ml, 50 pg/ml, 100 pg/ml, 200 pg/ml, 400 pg/ml, 800 pg/ml) are included in the test.

Samples are incubated for 1 h at room temperature.

Thereafter washing is performed on an automated ELISA washer as follows

7×250 µl washing buffer. The remaining buffer is removed.

Incubation with Detection Antibody

Working solutions of biotinylated secondary antibodies (clone mtm D7D7 specific for $p16^{INK4a}$, clone A5B4 for Ep-Cam and clone MAB 2083 specific for gamma-Catenin) are prepared by dilution of stock solutions.

100 μl of working solutions of biotinylated secondary antibodies are added to wells incubated with corresponding antigen and capture antibody. After incubation for 1h at RT, antibody solutions are removed and ELISA plates are washed by an automated ELISA washer 7×with 250 μl washing buffer.

Detection

Streptavidin-HRP-polymers (1 mg/ml) are pre-diluted 1:10 (4 μl+36 μl incubation buffer); Final incubation solution is prepared by dilution 1:300 in incubation buffer (0.1% BSA in PBS) to a final concentration of 0.33 μg/ml.

1001 μl of this solution are added to each well and incubated for 1 h at RT.

Thereafter, the buffer is removed and the plates are washed manually with 200 μl washing buffer per well 5 times.

Substrate Incubation

TMB-substrate is equilibrated to 25° C. for 1 h in the dark. 100 μl of substrate solution is added to each well.

The ELISA plates are incubated at 25° C. for exactly 15 min in the dark. Then the reaction is stopped by addition of 80 μl 2.5M $H_2SO_4$.

Within 5 min. after stopping the reaction OD 450 nm is determined. After evaluation of the results, each sample returns a value for the OD.

Evaluation of Results

For sample adequacy, OD values of all samples for gamma-Catenin have to exceed a defined threshold value to prove proper sampling of a minimum of cells. Furthermore to ensure proper sampling a threshold for the OD value of Ep-Cam indicating the presence of endocervical cells has to be exceeded.

For detection of dysplastic cells, OD values for $p16^{INK4a}$ have to exceed a defined threshold value to prove the presence of a minimum of p16-positive dysplastic cells.

Results of this experiment are given in Table 6.

TABLE 6

| No. of samples | $P16^{INK4a}$ | Gamma-Catenin | Conclusion |
|---|---|---|---|
| 3 | + | + | Sample is adequate; $p16^{INK4a}$ indicates the presence of dysplastic cells |
| 30 | − | + | Sample is adequate; absence of detectable $p16^{INK4a}$ indicates absence of dysplastic cells |
| 1 | − | − | Sample is inadequate; re-sampling necessary |

Comparison of OD values for $p16^{INK4a}$ and gamma-Catenin of 34 samples with corresponding threshold values revealed that 33 samples were adequate and could be further evaluated. From theses 33 samples, 30 samples were negative for $p16^{INK4a}$ and 3 were positive.

The ELISA results were compared to the diagnostic results of a Papanicolaou test (PAP test, cervical cytology) from the same patients. The cervical cytology were evaluated according to the Munich Classification II (1990). Pap II encompasses benign cells, cervicitis and metaplasia, Pap IV encompasses severe dysplasia and carcinoma in situ. It turned out that samples returning an OD for $p16^{INK4a}$ of greater than 0.9 in the ELISA correspond to samples, that are classified as dysplastic by the conventional cytological PAP test.

Applying OD 0.9 as threshold for the evaluation of the samples the ELISA results may be reported as follows.

TABLE 7

| Diagnosis/ELISA results | ELISA positive for $p16^{INK4a}$ | ELISA negative for $p16^{INK4a}$ |
|---|---|---|
| Pap II | 0 | 30 |
| Pap IV | 3 | 0 |
| Not enough cells | 0 | 1 |

The ELISA test is positive in all 3 samples (100%) from women having severe dysplasia and is negative in all 30 samples (100%) of women having no dysplasia. One sample only contained very few cells and therefore was excluded from evaluation, since sampling was inadequate.

The normalization of $p16^{INK4a}$ protein levels in solubilized patient samples with respect to a normalization marker characteristic for the presence of epithelial cells allows to assess diagnosis of dysplasias from the samples. The normalization in the present case allows especially to avoid false negative results due to inadequate sampling (for example total amount of patient material not sufficient to perform analysis, or the patient material is not taken at the correct anatomical location). The normalization is carried out in the testing format by applying a threshold value for the OD for the gamma-Catenin normalization marker determined in the ELISA above which the sample is to be classified as adequate. Below a certain threshold (corresponding to 200,000 squamous ectocervical cells) the sample does not contain an adequate amount of patient material. The use of a second normalization marker indicating the presence of endocervical cells provides further information about the adequacy of the sample. The normalization is carried out in the testing format by applying a threshold value for the OD for the Ep-Cam normalization marker determined in the ELISA above which the sample is to be classified as adequate. Below a certain threshold (corresponding to 2000 columnar endocervical cells) the sample does not contain an adequate amount of endocervical cells. (It must be understood that the threshold value applied in this example are adjusted to the particular reaction conditions. The value for the cells as well for OD may vary depending on the reaction conditions. Thus the values herein are intended to exemplify the conditions and not to limit the scope of the invention. Those of skill in the art know how an appropriate threshold value for a particular test format may be established.) The presence of endocervical cells provides the information that the swab or brush has had contact with the columnar epithelium of the endocervix and thus hints to a contact of the swab or brush with the transformation zone, where cervical dysplasia usually originates. In particular the detection of a certain amount of ectocervical cells (gamma-catenin) together with a certain amount of endocervical cells (Ep-Cam) provides with a high probability the information that the patient material was taken at the correct anatomical location (cervical transformation zone).

Using the threshold values evaluated in these experiments, cytological specimens of 300 patients were tested in the presented ELISA testing format. In this experiments the specimens identified as being dysplastic by cytological examination may also be identified as being dysplastic in the ELISA testing format.

Example 6

Detection of Cervical Intraepithelial Neoplasia in an ELISA Test Format

The 34 cervical swabs as already used in Example 5 provided in lysis buffer have been subjected to ELISA based detection of overexpression of HPV E7 Protein and one adequacy marker in solutions prepared from the cells contained in the swabs. The ELISA testing was performed as follows:

(A) Cell Lysis

Cervical swab brushes are given into 15 ml vessels, containing 2 ml of mtm lysis buffer. Cervical cells present in the brush are lysed for at least 20 h. The lysates of the cervical swab samples are then transferred in 2 ml tubes and are centrifuged at 4° C. (15 min at 28.000×g (16.600rpm High-speed Centrifuge JEC Multi RF)); Supernatant is transferred to a fresh tube. As the case may be the supernatant may be stored at −20° C.

(B) Performing the ELISA

Coating of ELISA-plates

Stock-solutions of E7-specific antibody clone NM2 and gamma-Catenin specific antibody clone 15 are diluted in PBS to give ready-to-use coating solution.

50 µl of each ready-to-use capture antibody coating solution is added to ELISA plates.

For coating, the plates are incubated overnight at 4° C.

Coating solutions are removed from the ELISA plates and the plates are rinsed using an automated ELISA washer as follows:

7×250 µl washing buffer (0.1% TWEEN®-20 (v/v) in PBS)

after removing remnants of the washing buffer, 300 µl blocking buffer (2% BSA in PBS) is added to each well. Plates are incubated for 1 h on a rocking device at ambient temperature.

Incubation with Samples

After removing the blocking buffer 100 µl of the lysed cell sample is added to each well. Lysates of HeLa-cells are used as positive control for antibodies specifically detecting gamma-Catenin; For purpose of calibration of the test, different concentrations of recombinant HPV 16 E7-protein, recombinant gamma-Catenin (0 pg/ml, 50 pg/ml, 100 pg/ml, 200 pg/ml, 400 pg/ml, 800 pg/ml) are included in the test.

Samples are incubated for 1 h at room temperature.

Thereafter washing is performed on an automated ELISA washer as follows

7×250 µl washing buffer. The remaining buffer is removed.

Incubation with detection antibody

Working solutions of biotinylated secondary antibodies (clone NM13 specific for HPV16 E7 protein and clone MAB 2083 specific for gamma-Catenin) are prepared by dilution of stock solutions.

100 µl of working solutions of biotinylated secondary antibodies are added to wells incubated with corresponding antigen and capture antibody. After incubation for 1 h at RT, antibody solutions are removed and ELISA plates are washed by an automated ELISA washer 7× with 250 µl washing buffer.

Detection

Streptavidin-HRP-polymers (1 mg/ml) are pre-diluted 1:10. (4 µl+36 µl incubation buffer); Final incubation solution is prepared by dilution 1:300 in incubation buffer (0.1% BSA in PBS) to a final concentration of 0.33 µg/ml.

100 µl of this solution are added to each well and incubated for 1 h at RT.

Thereafter, the buffer is removed and the plates are washed manually with 200 µl washing buffer per well 5 times.

Substrate Incubation

TMB-substrate is equilibrated to 25° C. for 1 h in the dark.

100 µl of substrate solution is added to each well.

The ELISA plates are incubated at 25° C. for exactly 15 min in the dark. Then the reaction is stopped by addition of 80 µl 2.5M H2SO4.

Within 5 min. after stopping the reaction OD 450 nm is determined. After evaluation of the results, each sample returns a value for the OD.

Evaluation of Results

For sample adequacy, OD values of all samples for gamma-Catenin have to exceed a defined threshold value to prove presence of a minimum of epithelial cells. (cf. Example 5)

For detection of dysplastic cells, OD values for HPV 16 E7 have to exceed a defined threshold value to prove the presence of a minimum of transformed cells. The threshold depends on the ELISA conditions applied and was set as OD 0.7 in our test format.

Comparison of OD values for HPV 16 E7, gamma-Catenin of 34 samples with threshold values revealed that the 33 samples proven to contain epithelial cells by means of detection of gamma-Catenin.

Although the invention has been described with reference to the presently preferred embodiments, it should be understood that various modifications could be made without departing from the scope of the invention.

---

What is claimed is:

1. A method for detecting cervical dysplasia, cervical cancer or high grade cervical intraepithelial neoplasia in human cervical samples comprising:

preparing a sample solution by solubilizing a human cervical sample in a lysis buffer;

determining the level of p16$^{INK4a}$ within the sample solution and comparing the determined level with the level of p16$^{INK4a}$ in a normal human cervical sample;

determining the level of at least one normalization marker characteristic for the presence of ectocervical or endocervical cells within the sample solution, wherein said normalization marker is gamma-Catenin comprising SEQ ID NO: 1; Ep-Cam comprising SEQ ID NO: 2; E-Cadherin comprising SEQ ID NO: 3; alpha-1 Catenin comprising SEQ ID NO: 4; alpha-2 Catenin comprising SEQ ID NO: 5; beta-Catenin comprising SEQ ID NO: 6; Involucrin comprising SEQ ID NO: 7; or p120 comprising SEQ ID NO: 8;

determining a threshold value of the normalization marker by measuring the level of the normalization marker in a control sample solution containing an amount of ectocervical cells or endocervical cells;

comparing the level of the at least one normalization marker determined within the sample solution with the threshold value of the normalization marker; and determining that said human cervical sample contains cervical dysplastic cells, cervical cancer cells, or high grade cervical intraepithelial neoplastic cells when the determined level of the at least one normalization marker in the sample solution is elevated above the threshold value and the determined level of p16$^{INK4a}$ in the sample solution is elevated above the level of p16$^{INK4a}$ in the normal human cervical sample.

2. The method according to claim 1, wherein said method is used in early detection or primary screening tests of cervical lesions.

3. The method according to claim 1, wherein said human cervical sample is a swab, a secretion, an aspirate, a lavage, a cell, a tissue, a biopsy or a body fluid.

4. The method according to claim 1, wherein said method comprises determining the level of Ep-Cam comprising SEQ ID NO: 2.

5. The method according to claim 1, wherein said method comprises determining the level of at least one normalization marker selected from the group consisting of gamma-Catenin comprising SEQ ID NO: 1; E-Cadherin comprising SEQ ID NO: 3; alpha-1 Catenin comprising SEQ ID NO: 4; alpha-2 Catenin comprising SEQ ID NO: 5; beta-Catenin comprising SEQ ID NO: 6; Involucrin comprising SEQ ID NO: 7; and p120 comprising SEQ ID NO: 8.

6. The method according to claim 1, wherein said method comprises determining the level of gamma-Catenin comprising SEQ ID NO: 1.

7. A method for determining the presence of cervical dysplasia, cervical cancer or high grade cervical intraepithelial neoplasia in human cervical samples comprising:
    preparing a sample solution by solubilizing a human cervical sample in a lysis buffer;
    determining the level of p16$^{INK4a}$ within the sample solution and comparing the determined level with the level of p16$^{INK4a}$ in a normal human cervical sample;
    determining the presence of at least one normalization marker characteristic for the presence of ectocervical or endocervical cells within the sample solution, wherein said normalization marker is gamma-Catenin comprising SEQ ID NO: 1; Ep-Cam comprising SEQ ID NO: 2; E-Cadherin comprising SEQ ID NO: 3; alpha-1 Catenin comprising SEQ ID NO: 4; alpha-2 Catenin comprising SEQ ID NO: 5; beta-Catenin comprising SEQ ID NO: 6; Involucrin comprising SEQ ID NO: 7; or p120 comprising SEQ ID NO: 8; and
    determining that (i) said human cervical sample contains cervical dysplastic cells, cervical cancer cells, or high grade cervical intraepithelial neoplastic cells when at least one of said normalization markers is present in the sample solution and the determined level of p16$^{INK4a}$ in the sample solution is elevated above the level of p16$^{INK4a}$ in the normal human cervical sample; or (ii) said human cervical body sample is inadequate for said determination of the presence of cervical dysplasia, cervical cancer or high grade cervical intraepithelial neoplasia when none of said normalization markers is present within said sample solution.

8. The method according to claim 7, wherein said method is used in early detection or primary screening tests of cervical lesions.

9. The method according to claim 7, wherein said human cervical sample is a swab, a secretion, an aspirate, a lavage, a cell, a tissue, a biopsy or a body fluid.

10. The method according to claim 7, wherein said method comprises determining the level of Ep-Cam comprising SEQ ID NO: 2.

11. The method according to claim 7, wherein said method comprises determining the level of at least one normalization marker selected from the group consisting of gamma-Catenin comprising SEQ ID NO: 1; E-Cadherin comprising SEQ ID NO: 3; alpha-1 Catenin comprising SEQ ID NO: 4; alpha-2 Catenin comprising SEQ ID NO: 5; beta-Catenin comprising SEQ ID NO: 6; Involucrin comprising SEQ ID NO: 7; and p120 comprising SEQ ID NO: 8.

12. The method according to claim 7, wherein said method comprises determining the level of gamma-Catenin comprising SEQ ID NO: 1.

* * * * *